United States Patent
Lukin

(10) Patent No.: US 10,882,861 B2
(45) Date of Patent: Jan. 5, 2021

(54) PURINE NUCLEOTIDE DERIVATIVES

(71) Applicant: The Research Foundation for the State University of New York, Albany, NY (US)

(72) Inventor: Mark Lukin, East Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 206 days.

(21) Appl. No.: 16/302,857

(22) PCT Filed: May 19, 2017

(86) PCT No.: PCT/US2017/033498
§ 371 (c)(1),
(2) Date: Nov. 19, 2018

(87) PCT Pub. No.: WO2017/201382
PCT Pub. Date: Nov. 23, 2017

(65) Prior Publication Data
US 2019/0300532 A1    Oct. 3, 2019

Related U.S. Application Data

(60) Provisional application No. 62/339,714, filed on May 20, 2016.

(51) Int. Cl.
| | | |
|---|---|---|
| *C07H 19/04* | (2006.01) | |
| *C07H 19/20* | (2006.01) | |
| *C07D 473/16* | (2006.01) | |
| *C07D 473/18* | (2006.01) | |
| *C07H 21/04* | (2006.01) | |
| *C07D 487/04* | (2006.01) | |

(52) U.S. Cl.
CPC ......... *C07D 473/16* (2013.01); *C07D 473/18* (2013.01); *C07D 487/04* (2013.01); *C07H 19/20* (2013.01); *C07H 21/04* (2013.01)

(58) Field of Classification Search
None
See application file for complete search history.

(56) References Cited

U.S. PATENT DOCUMENTS 4,258,033 A * 3/1981 Marumoto ............. C07H 19/16
514/45

FOREIGN PATENT DOCUMENTS

JP    55053299    4/1980

OTHER PUBLICATIONS

Monique L.M. De Poll et al., "An unusual dearomatized adduct formed by reaction of 4'-fluoro-4-(acetylamino)biphenyl N-sulfate with deoxyadenosine," Chemical Research in Toxicology, 1991.
Monique L.M. De Poll et al., "The role of sulfation in the metabolic activation of N-hydroxy-4'-fluoro-4-acetylaminobiphenyl," Carcinogenesis, 1989, vol. 10, No. 12.
Takeji Takamura-Enya et al., "Palladium-Catalyzed Direct N-Arylation of Nucleosides, Nucleotides, and Oligonucleotides for Efficient Preparation of dG-$N^2$ Adducts with Carcinogenic Amino-/Nitroarenes," Journal of Organic Chemistry, 2006, vol. 71, No. 15.
International Search Report dated Sep. 7, 2017 in connection with PCT International Application No. PCT/US2017/033,498.
Written Opinion of the International Searching Authority dated Sep. 7, 2017 in connection with PCT International Application No. PCT/US2017/033,498.

* cited by examiner

Primary Examiner — Patrick T Lewis
(74) Attorney, Agent, or Firm — Gary J. Gershik

(57) ABSTRACT

The present invention provides a compound having the structure:

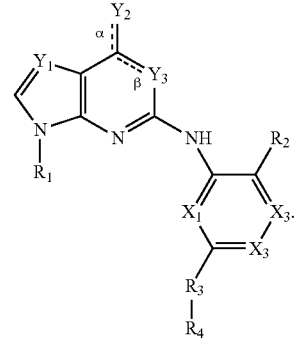

20 Claims, 6 Drawing Sheets

|   | Sequence | $T_m$ | $T_m$(ctrl) | $\Delta T_m$ | X |
|---|---|---|---|---|---|
| I | CGTATXTATGC<br>GCATACATACG | 57.5 | 44.1 | 13.4 | PDZdG |
| II | CGTACXCATGC<br>GCATGCGTACG | 60.5 | 55.5 | 6.0 | PDZdG |
| III | CGTATGTATGC<br>GCATAXATACG | 49.3 | 44.1 | 5.2 | "G-clamp" |
| IV | CGTACGCATGC<br>GCATGXGTACG | 67.3 | 55.5 | 11.8 | "G-clamp" |
| V | CGTATXTATGC<br>GCATACATACG | 62.9 | 44.1 | 18.8 | MePizPDZdG |
| VI | CGTACXCATGC<br>GCATGCGTACG | 68.5 | 55.5 | 13.0 | MePizPDZdG |
| VII | CGTATXTATGC<br>GCATATATACG | 53.5 | 37.3 | 16.2 | PDZdA |

Fig. 2

|                              | I      | Parent              |
| ---------------------------- | ------ | ------------------- |
| $\Delta H$, kcal/mol         | -79    | -67                 |
| $\Delta S$, kcal/mol·K       | -0.21  | -0.19               |
| $\Delta G_{298}$, kcal/mol   | -15.5  | -11.9 ($\Delta\Delta G$=3.6) |

Fig. 4

PURINE NUCLEOTIDE DERIVATIVES

CROSS-REFERENCE TO RELATED APPLICATIONS

This application is a § 371 national stage of PCT International Application No. PCT/US2017/033,498, filed May 19, 2017, and claims the benefit of U.S. Provisional Application No. 62/339,714, filed May 20, 2016, the content of each of which are hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Development of novel oligonucleotide analogs that possess enhanced binding affinity and selectivity in the formation of duplexes with complementary DNA sequences would be instrumental for numerous applications, from biotechnology and medicine to material sciences and nanotechnology. A number of artificial oligonucleotides have been developed that stabilize duplexes by maximizing stacking interaction and by forming additional hydrogen bonds, or by minimizing electrostatic repulsion between DNA strands (Lin, K-Y. et al. 1998; Nielden, P. E. et al. 1991). The nucleotide analog ("G-clamp") utilizing these effects was developed and is capable of binding to complementary guanine with high affinity and specificity (Lin, K-Y. et al. 1998). However, its stabilizing effect significantly depends on the sequence context, and in some cases is very moderate (Ortega J-A. et al. 2007). No nucleotides with comparable affinity towards purines are currently known.

Other oligonucleotide analogs are currently used to increase affinity of oligonucleotides to complementary DNA sequences. These compounds include: (1) minor groove binder adducts (MGBs), (2) ethynyl derivatives of pyrimidine nucleotides, and (3) oligonucleotide analogs with modified sugar-phosphate backbone (the most notable examples are locked nucleic acids, or LNAs, and peptide nucleic acids, or PNAs).

SUMMARY OF THE INVENTION

The present invention provides a compound having the structure:

wherein
$\alpha$ is a bond and is present or absent,
$\beta$ is a bond and is present or absent,
wherein when $\alpha$ is present, then $\beta$ is absent and when $\beta$ is present, then $\alpha$ is absent;
$Y_1$ is N or $CR_5$,
wherein $R_5$ is aminoalkyl;
$Y_2$ is O, $NH_2$, $NHR_6$ or $NH-PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_1$ is a substituted tetrahydrofuran;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

The present invention provides a nucleotide or nucleoside containing the following structural moiety:

wherein
$\alpha$ is a bond and is present or absent,
$\beta$ is a bond and is present or absent,
wherein when $\alpha$ is present, then $\beta$ is absent and when $\beta$ is present, then $\alpha$ is absent;
$Y_1$ is N or $CR_5$,
wherein $R_5$ is aminoalkyl;
$Y_2$ is O, $NH_2$, $NHR_6$ or $NH-PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

The present invention provides an oligonucleotide or polynucleotide containing the following structural moiety:

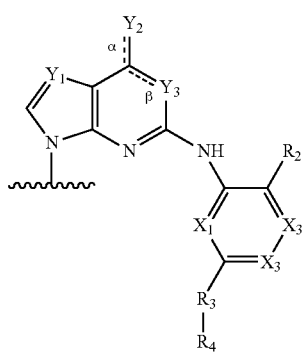

wherein
α is a bond and is present or absent,
β is a bond and is present or absent,
wherein when α is present, then β is absent and when β is present, then α is absent;
$Y_1$ is N or $CR_5$,
wherein $R_5$ is aminoalkyl;
$Y_2$ is O, $NH_2$ or $NHR_6$,
wherein $R_6$ is alkyl, aminoalkyl or —C(O)-alkyl;
$Y_3$ is N or NH;
$X_1$ is N or CH;
$X_2$ is N or CH;
$X_3$ is N or CH;
$Y_2$ is O, $NH_2$, $NHR_6$ or NH-$PG_1$,
wherein $R_6$ is alkyl, aminoalkyl or —C(O)-alkyl, and $PG_1$ is a suitable amine protecting group;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

The present invention provides a peptide nucleic acid containing the following structural moiety:

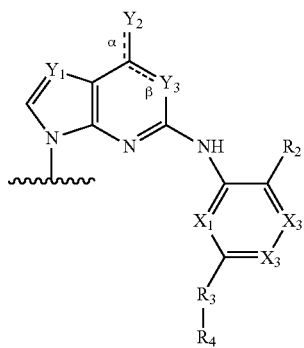

wherein
α is a bond and is present or absent,
β is a bond and is present or absent,
wherein when α is present, then β is absent and when β is present, then α is absent;
$Y_1$ is N or $CR_5$,
wherein $R_5$ is aminoalkyl;
$Y_2$ is O, $NH_2$, $NHR_6$ or NH-$PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

BRIEF DESCRIPTION OF THE FIGURES

FIG. 2: Melting temperatures of DNA duplexes containing the PDZ-dG (X) or PDZ-dA (Y) nucleotides vs the parent duplexes. The data for "G-clamp" duplexes are provided for comparison.

FIG. 4: Thermodynamic parameters the duplex CGTATXTATGC/GCATACATACG (I), where X is a PDZdG nucleotide relative to its parent dG•dC undecamer

DETAILED DESCRIPTION OF THE INVENTION

Figure 1:
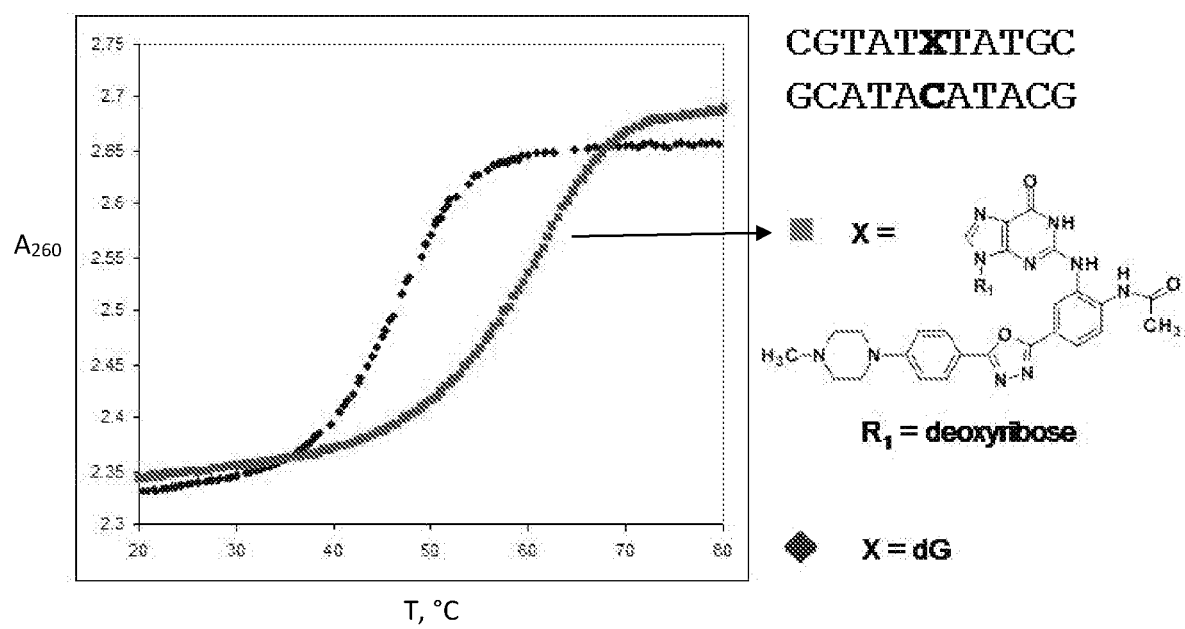
FIG. 1: Thermally induced dissociation profiles (Absorbance at 260 nm vs temperature) of the 11-mer duplex V containing a central MePizPDZ-dG•dC base pair (blue diamonds) and its dG•dC parent (pink squares). The structure of the modified dG analog is shown on the right.

The present invention provides a compound having the structure:

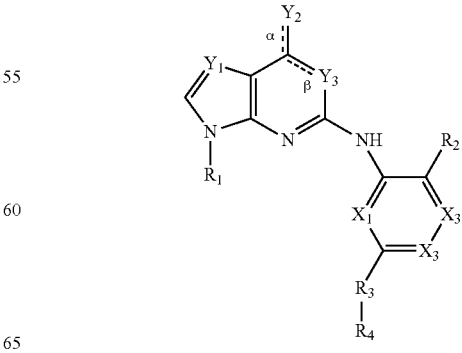

wherein

α is a bond and is present or absent,

β is a bond and is present or absent, wherein when α is present, then β is absent and when β is present, then α is absent;

$Y_1$ is N or $CR_5$, wherein $R_5$ is aminoalkyl;

$Y_2$ is O, $NH_2$, $NHR_6$ or $NH-PG_1$, wherein $R_6$ is alkyl, aminoalkyl or —C(O)-alkyl, and $PG_1$ is a suitable amine protecting group;

$Y_3$ is N or NH;

$X_1$ is N or CH;

$X_2$ is N or CH;

$X_3$ is N or CH;

$R_1$ is a substituted tetrahydrofuran;

$R_2$ is H, $NH_2$ or NHC(O)—$R_7$, wherein $R_7$ is alkyl, aryl, alkylaryl or aminoalkyl;

$R_3$ is present or absent and when present is —C(O)—, —C(O)NH—, —NH(O)C— or —N=N—; and $R_4$ is a substituted five or six-membered aryl or heteroaryl, wherein the substitution on the six-membered aryl is other than fluorine substitution.

In some embodiments, the compound wherein

α is a bond and is present or absent,

β is a bond and is present or absent, wherein when α is present, then β is absent and when β is present, then α is absent;

$Y_1$ is N or $CR_5$, wherein $R_5$ is aminoalkyl;

$Y_2$ is O, $NH_2$, $NHR_6$ or $NH-PG_1$, wherein $R_6$ is alkyl, aminoalkyl or —C(O)-alkyl, and $PG_1$ is a suitable amine protecting group;

$Y_3$ is N or NH;

$X_1$ is N or CH;

$X_2$ is N or CH;

$X_3$ is N or CH;

$R_1$ is a substituted tetrahydrofuran;

$R_2$ is NHC(O)—$R_7$, wherein $R_7$ is alkyl;

$R_3$ is present or absent and when present is —C(O)—, —C(O)NH—, —NH(O)C— or —N=N—; and $R_4$ is a substituted five or six-membered aryl or heteroaryl, wherein the substitution on the six-membered aryl is other than fluorine substitution.

In some embodiments, the compound wherein $Y_1$ is N.

In some embodiments, the compound wherein $Y_1$ is $CR_5$, wherein $R_5$ is aminoalkyl.

In some embodiments, the compound wherein $R_5$ is —$CH_2$—$NH_2$.

In some embodiments, the compound wherein $Y_2$ is O.

In some embodiments, the compound wherein $Y_2$ is $NH_2$.

In some embodiments, the compound wherein $Y_2$ is $NHR_6$, wherein $R_6$ is alkyl, alkyl-$NH_2$ or —C(O)-alkyl.

In some embodiments, the compound wherein $Y_2$ is $NH-PG_1$.

In some embodiments, the compound wherein $PG_1$ is —C(O)-iPr, —C(O)-phenyl or —C(O)—$CH_2$—O-phenyl.

In some embodiments, the compound wherein $Y_3$ is N.

In some embodiments, the compound wherein $Y_3$ is NH.

In some embodiments, the compound having the structure:

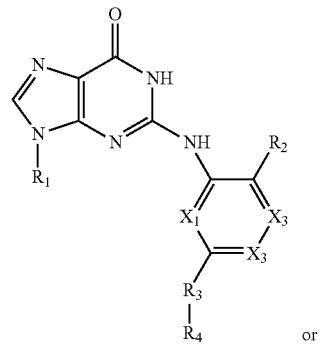

or

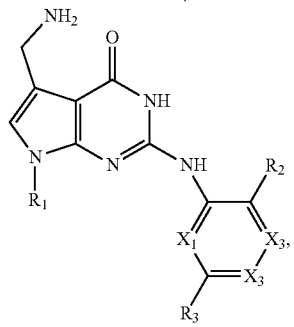

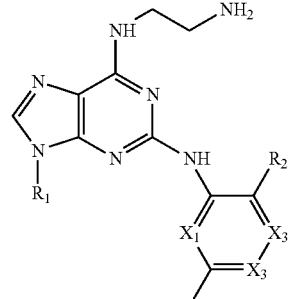

or

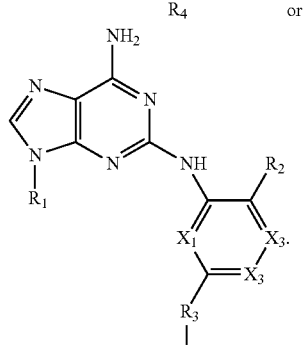

In some embodiments, the compound wherein one of $X_1$, $X_2$ or $X_3$ is N and the other two of $X_1$, $X_2$ or $X_3$ are CH.

In some embodiments, the compound wherein two of $X_1$, $X_2$ or $X_3$ is N and the other one of $X_1$, $X_2$ or $X_3$ are CH.

In some embodiments, the compound wherein $R_2$ is H.

In some embodiments, the compound wherein $R_2$ is NHC(O)—$R_7$, wherein $R_7$ is alkyl, aryl or alkylaryl.

In some embodiments, the compound wherein $R_7$ is $CH_3$, $CH_2CH_3$, $CH_2$ $(CH_3)_2$, $CH_2CH_2CH_2CH_3$, phenyl or benzyl.

In some embodiments, the compound wherein $R_3$ is absent.

In some embodiments, the compound wherein $R_3$ is present and is —C(O)NH—, —NH(O)C— or —N=N—.

In some embodiments, the compound wherein $R_4$ has the structure:

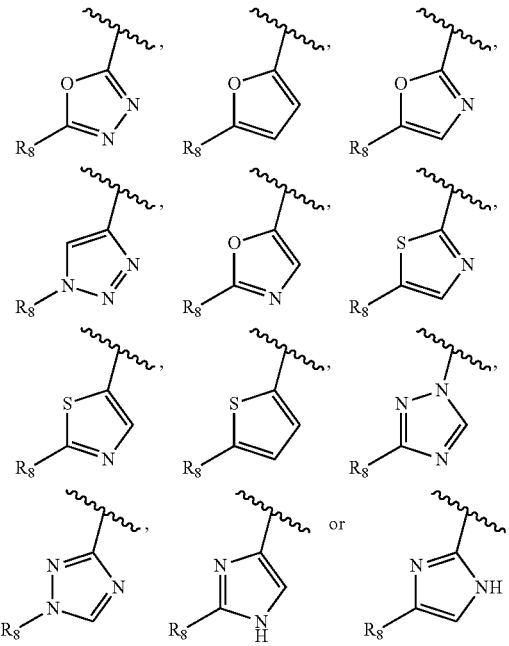

wherein $R_8$ is alkyl, alkenyl, alkynyl, aryl, substituted aryl, heteroaryl, substituted heteroaryl, heteroalkyl or heterocycloalkyl.

In some embodiments, the compound wherein $R_8$ is aryl, substituted aryl, heteroaryl, substituted heteroaryl, heteroalkyl or heterocycloalkyl.

In some embodiments, the compound wherein $R_8$ is a substituted aryl or substituted heteroaryl.

In some embodiments, the compound wherein $R_8$ has the structure:

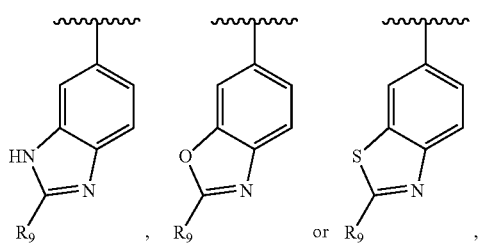

wherein $R_9$ is alkyl, aryl, substituted aryl, heteroaryl, substituted heteroaryl or heterocycloalkyl.

In some embodiments, the compound wherein $R_8$ has the structure:

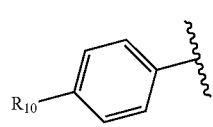

wherein $R_{10}$ is alkyl, aminoalkyl, aryl, substituted aryl, heteroaryl, substituted heteroaryl or heterocycloalkyl.

In some embodiments, the compound wherein $R_8$ has the structure:

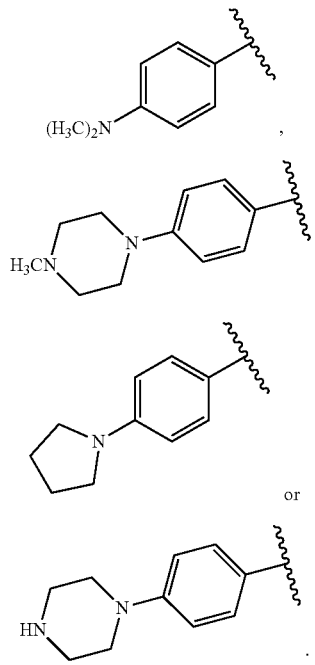

In some embodiments, the compound wherein $R_4$ has the structure:

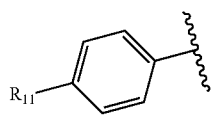

wherein $R_{11}$ is alkyl, aminoalkyl, aryl, substituted aryl, heteroaryl, substituted heteroaryl or heterocycloalkyl.

In some embodiments, the compound wherein $R_4$ has the structure:

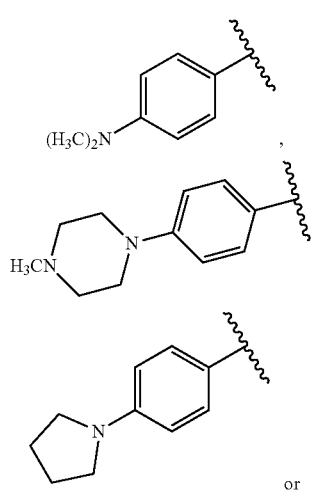

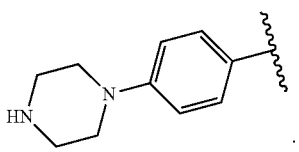
In some embodiments, the compound having the structure:
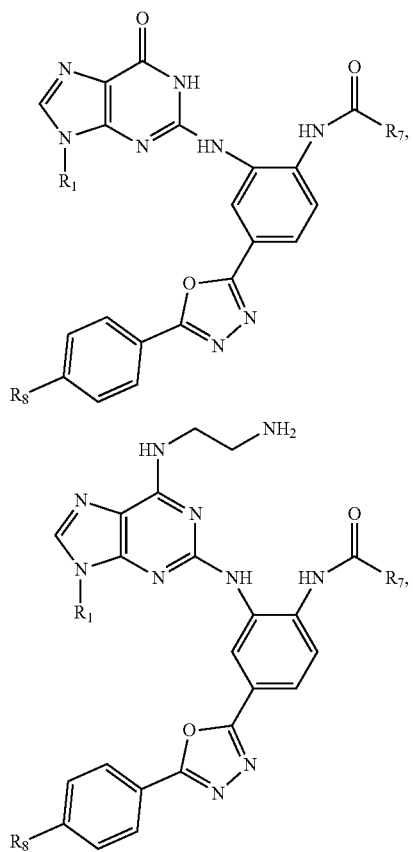
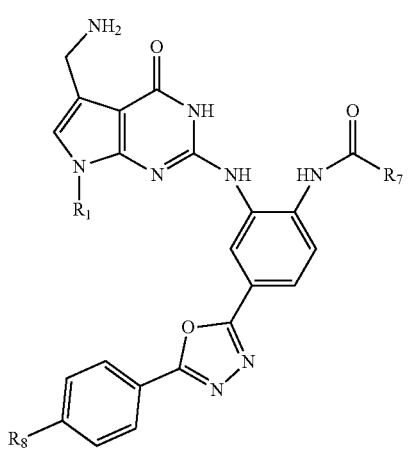
or
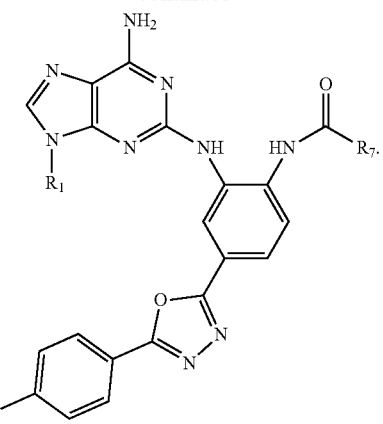
In some embodiments, the compound having the structure:
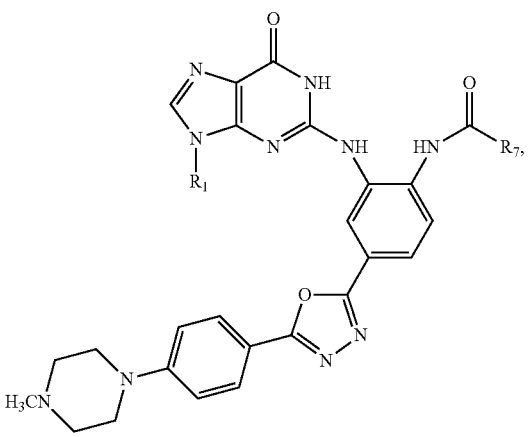
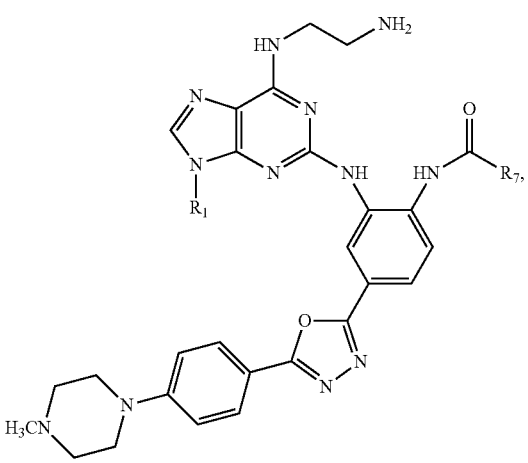

-continued
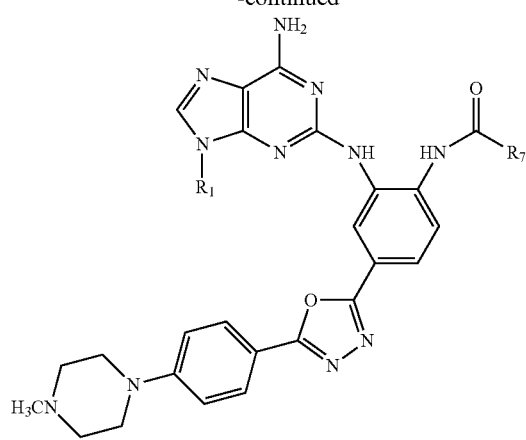
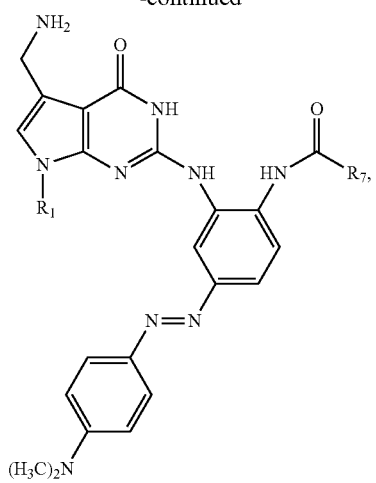
or
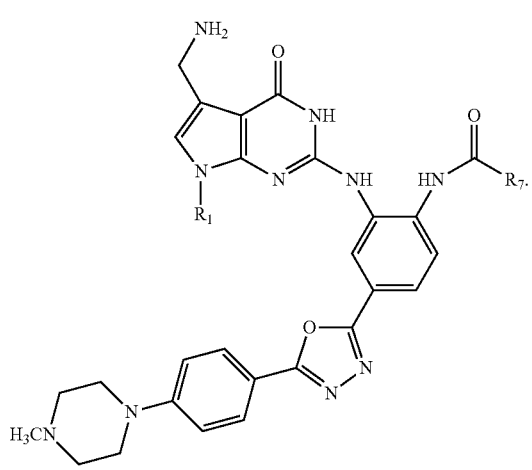
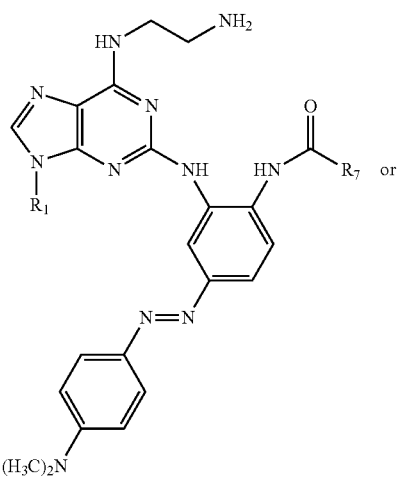
In some embodiments, the compound having the structure:
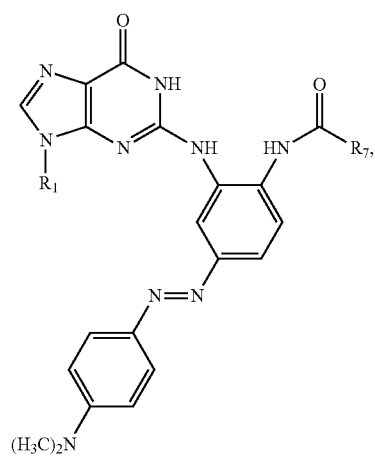
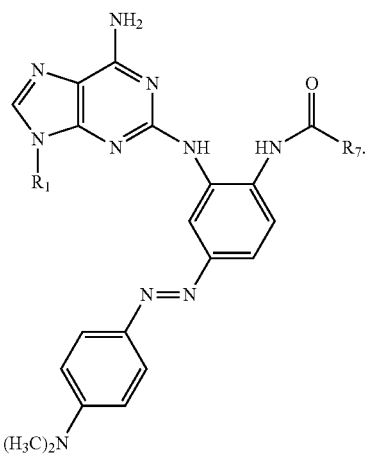

In some embodiments, the compound having the structure:
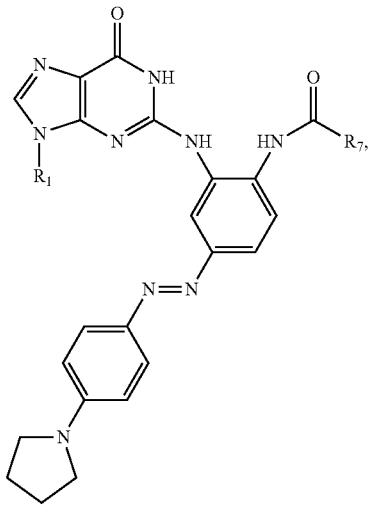
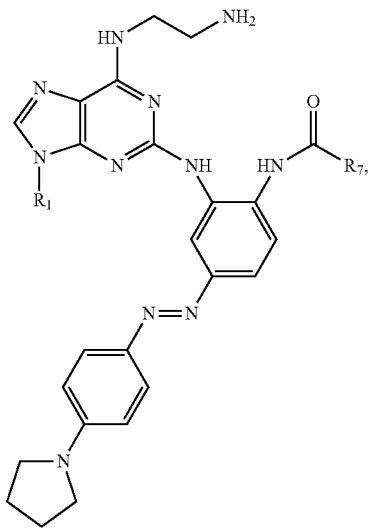
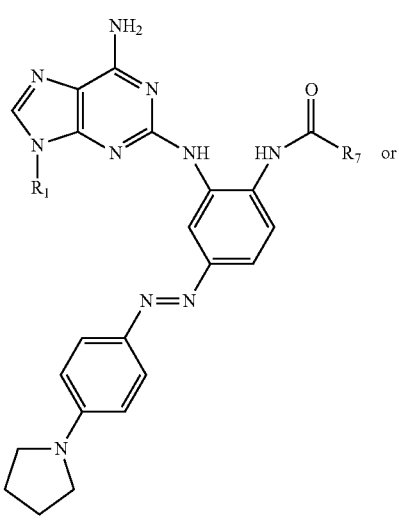
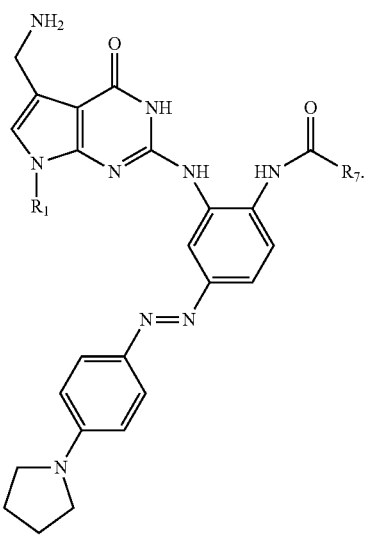
In some embodiments, the compound having the structure:
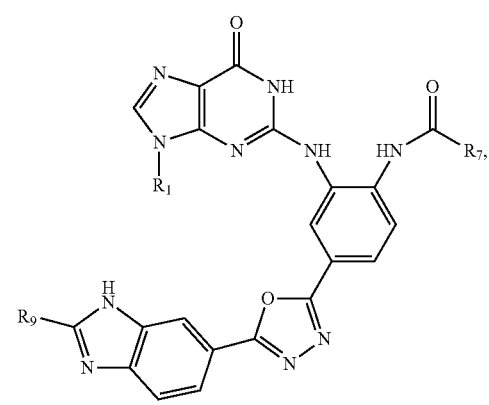
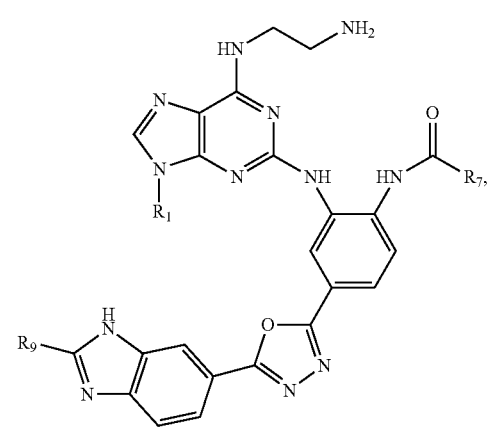

-continued

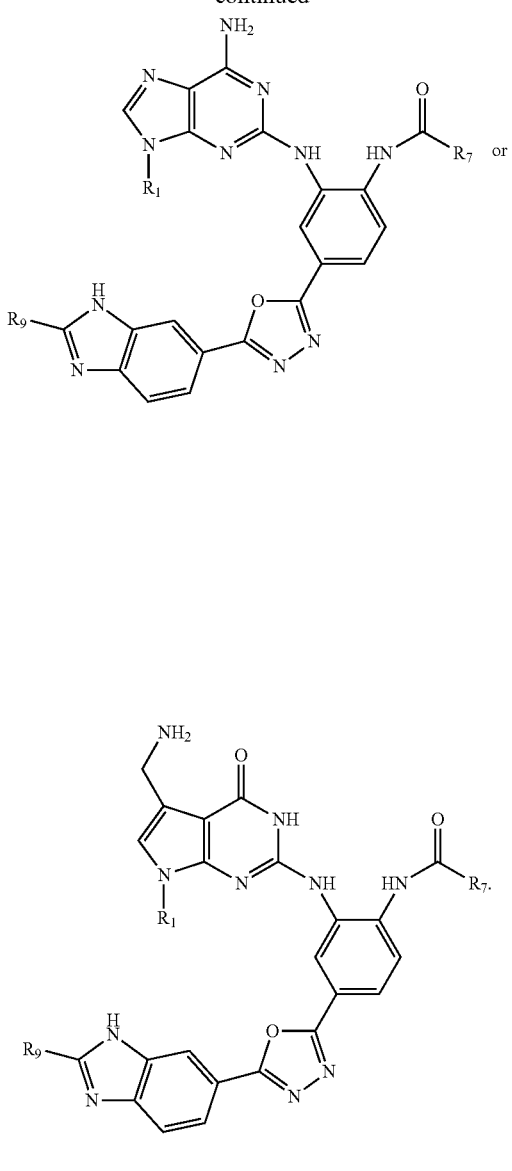

In some embodiments, the compound having the structure:

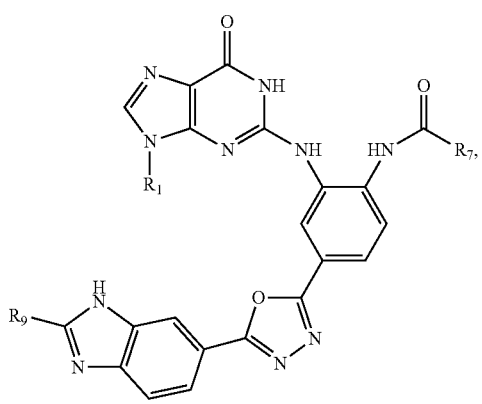

-continued

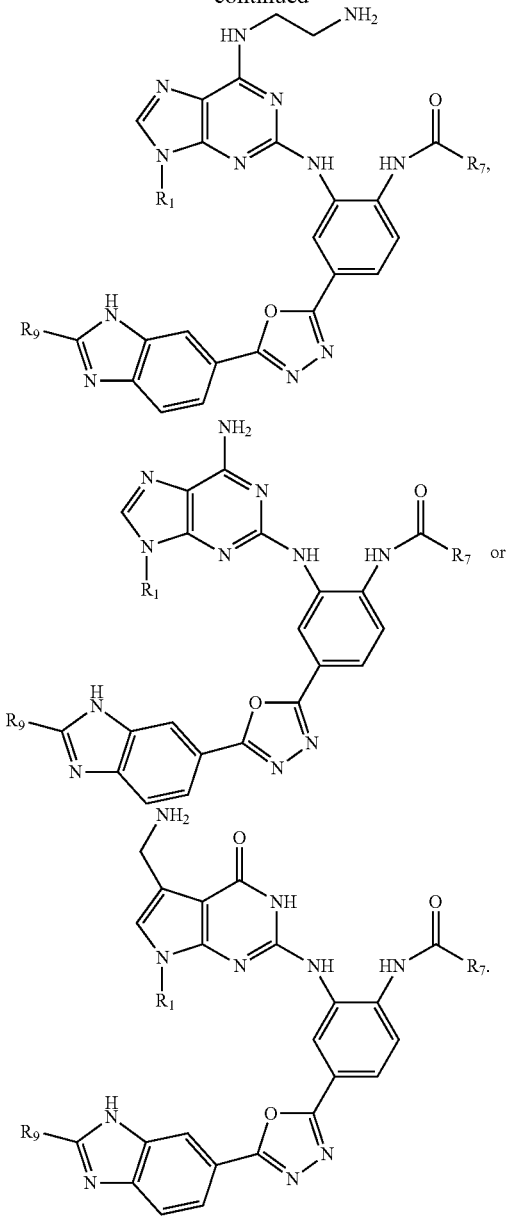

In some embodiments, the compound wherein $R_7$ is $CH_3$.
In some embodiments, the compound wherein $R_7$ is $CH_2CH_3$.
In some embodiments, the compound wherein $R_7$ is phenyl or benzyl.
In some embodiments, the compound wherein $R_1$ has the structure:

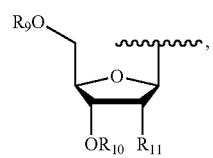

wherein
$R_9$ is H or $PG_2$;
$R_{10}$ is H or $PG_3$;
$R_{11}$ is H, OH or O-$PG_4$, wherein PG$_2$, PG$_3$ and PG$_4$ are each, independently, a suitable hydroxyl protecting group.

In some embodiments, the compound wherein R$_9$ is H.

In some embodiments, the compound wherein R$_9$ is PG$_2$, wherein the PG$_2$ is a trityl, monomethoxy trityl (MMT), dimethoxytrityl (DMT), acetyl benzoyl, isobutyl, or 5'-O-(α-methyl-6-nitropiperonyloxycarbonyl) (MeNPOC).

In some embodiments, the compound wherein R$_{11}$ is H.

In some embodiments, the compound wherein R$_{11}$ is OH.

In some embodiments, the compound wherein R$_{11}$ is O-PG$_4$, wherein the PG$_4$ is a tert-butyldimethylsilyl (TBDMS or TBS), triisopropylsilyloxymethyl (TOM), bis(2-acetoxyethoxy)methyl (ACE) or thiomorpholine-4-carbothioate (TC).

In some embodiments, the compound wherein R$_{10}$ is H.

In some embodiments, the compound wherein R$_{10}$ is PG$_3$ wherein the PG$_3$ is a phosphoramidite group.

In some embodiments, the compound wherein R$_{10}$ has the structure:

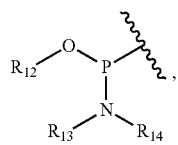

wherein

R$_{12}$ is cyanoethyl, trichloroethyl, methyl, phenyl, benzyl, dimethyltrichloroethyl, chlorophenyl, 2-phenylethyl or a substituted aryl; and R$_{13}$ and R$_{14}$ are each isopropyl or methyl or combine to form a morpholino.

In some embodiments, the compound wherein R$_{10}$ has the structure:

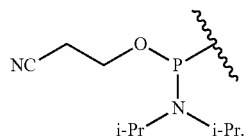

In some embodiments, the compound having the structure:

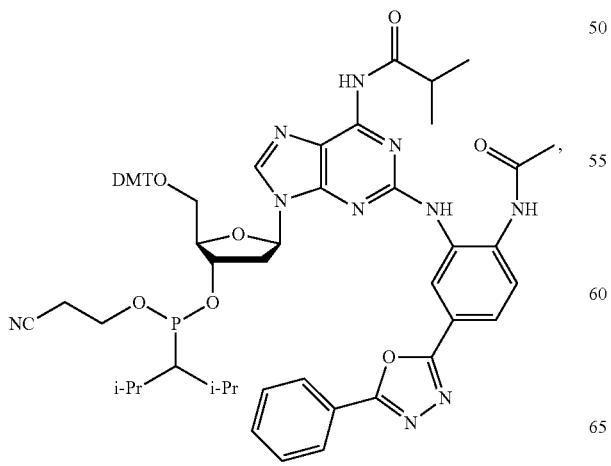

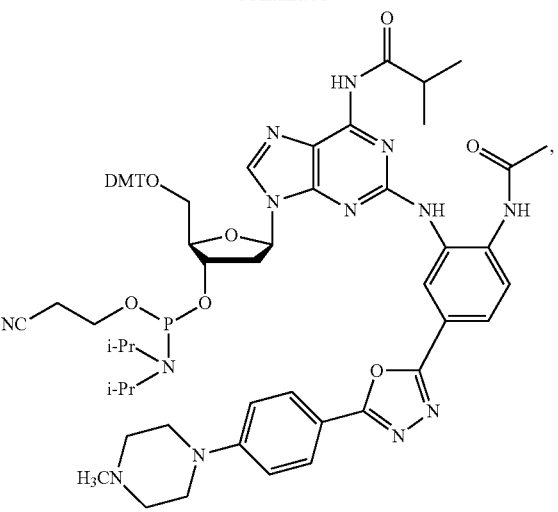

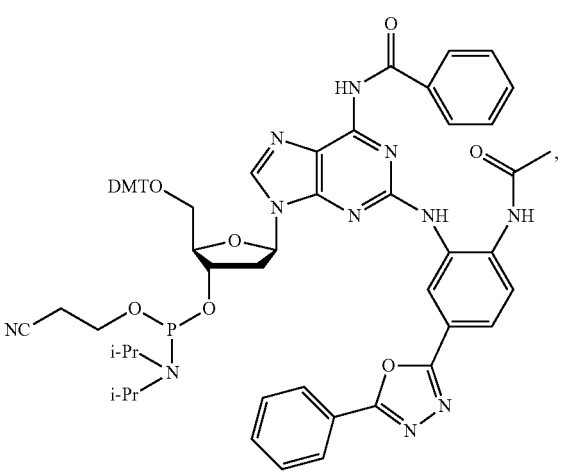

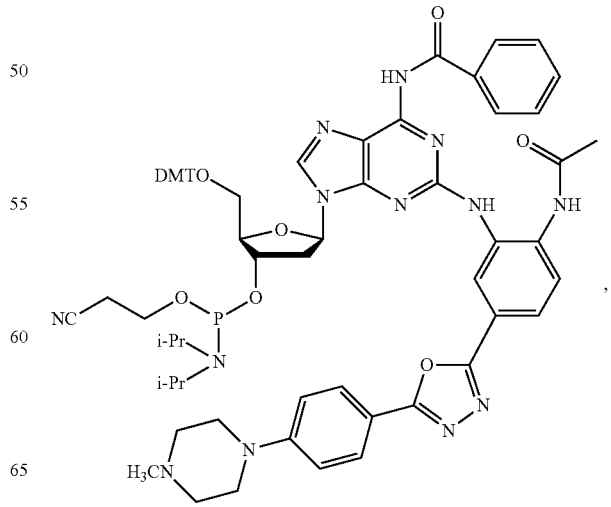

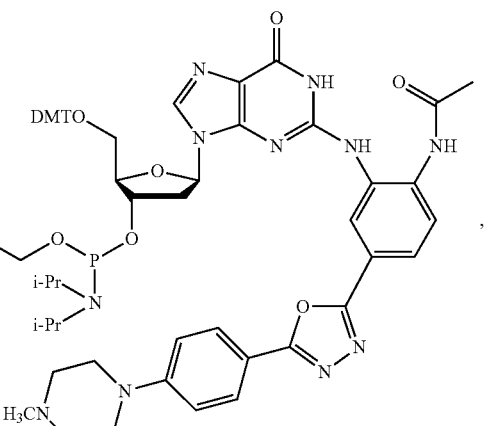
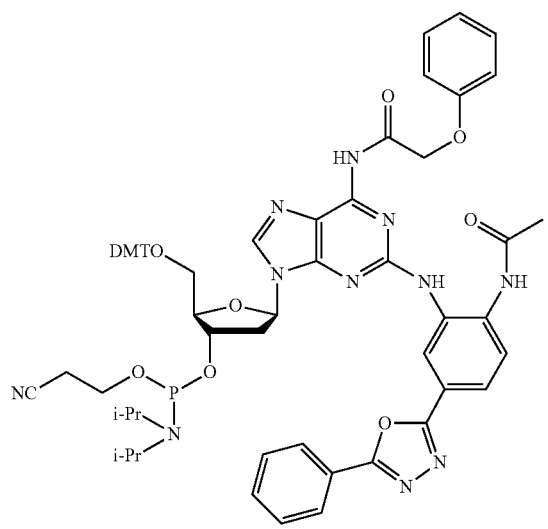
or
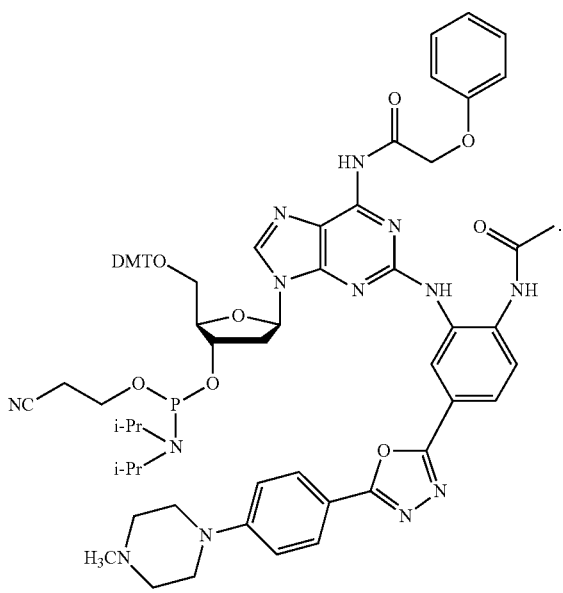
In some embodiments, the compound having the structure:
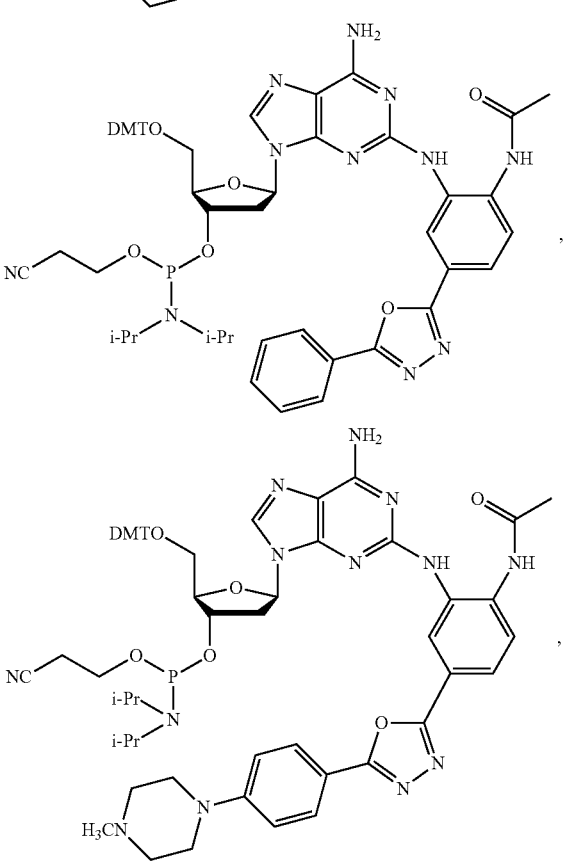
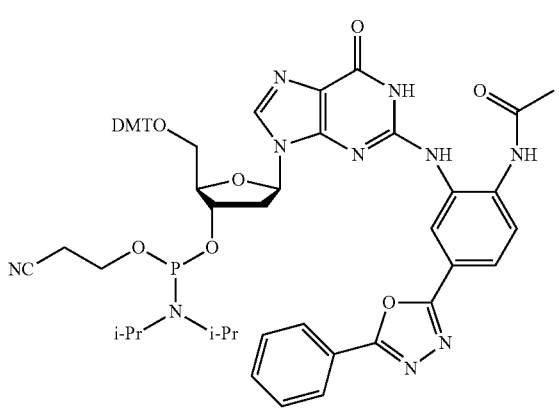
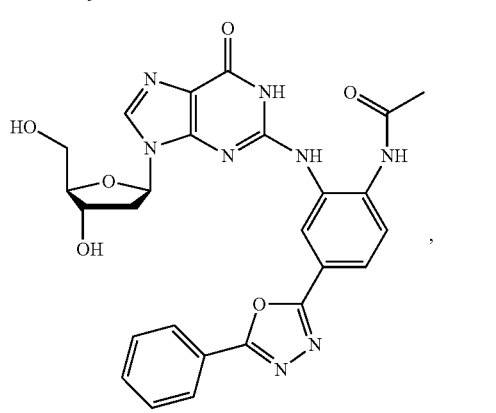

-continued

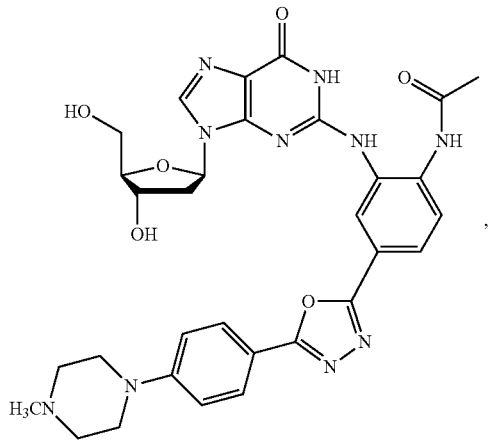

,

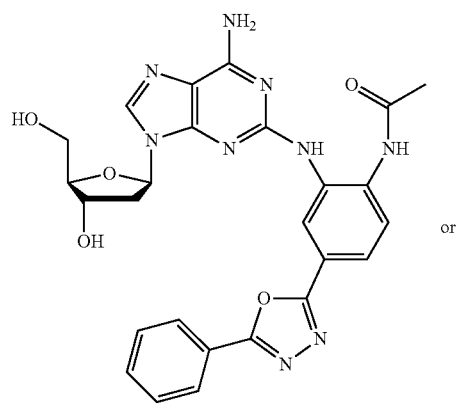

or

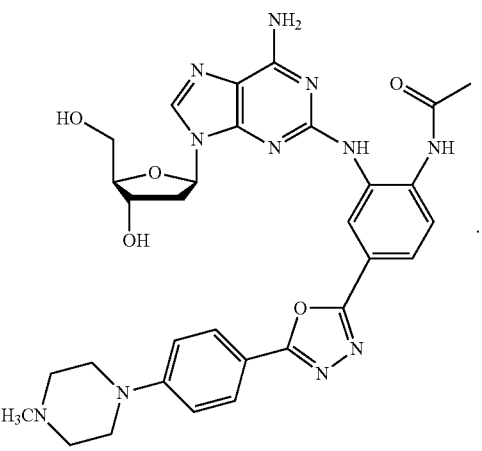

.

The present invention provides a nucleotide or nucleoside containing the following structural moiety:

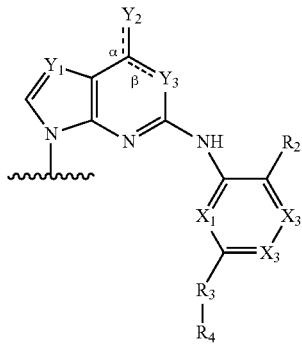

wherein
α is a bond and is present or absent,
β is a bond and is present or absent,
wherein when α is present, then β is absent and when β is present, then α is absent;
$Y_1$ is N or $CR_5$,
wherein $R_5$ is aminoalkyl;
$Y_2$ is O, $NH_2$, $NHR_6$ or $NH\text{-}PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N═N—; and
$R_4$ is a substituted five or six-membered aryl or heteroaryl, wherein the substitution on the six-membered aryl is other than fluorine substitution.

The present invention provides an oligonucleotide or polynucleotide containing the following structural moiety:

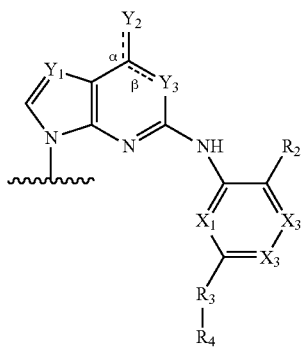

wherein
α is a bond and is present or absent,
β is a bond and is present or absent,
wherein when α is present, then β is absent and when β is present, then α is absent;
$Y_1$ is N or $CR_5$,
wherein $R_5$ is aminoalkyl;
$Y_2$ is O, $NH_2$ or $NHR_6$,
wherein $R_6$ is alkyl, aminoalkyl or —C(O)-alkyl;
$Y_3$ is N or NH;
$X_1$ is N or CH;
$X_2$ is N or CH;

X₃ is N or CH;

Y₂ is O, NH₂, NHR₆ or NH-PG₁, wherein R₆ is alkyl, aminoalkyl or —C(O)-alkyl, and PG₁ is a suitable amine protecting group;

R₂ is H, NH₂ or NHC(O)—R₇, wherein R₇ is alkyl, aryl, alkylaryl or aminoalkyl;

R₃ is present or absent and when present is —C(O)—, —C(O)NH—, —NH(O)C— or —N=N—; and R₄ is a substituted five or six-membered aryl or heteroaryl, wherein the substitution on the six-membered aryl is other than fluorine substitution.

The present invention provides a peptide nucleic acid containing the following structural moiety:

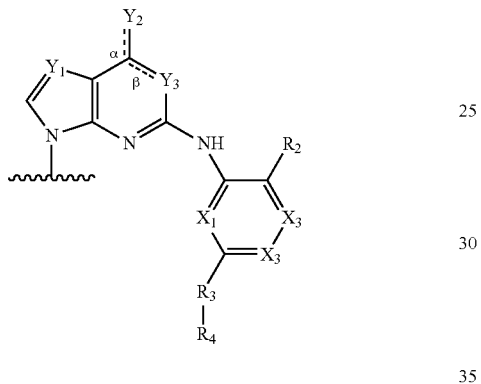

wherein

α is a bond and is present or absent,

β is a bond and is present or absent, wherein when α is present, then β is absent and when β is present, then α is absent;

Y₁ is N or CR₅, wherein R₅ is aminoalkyl;

Y₂ is O, NH₂, NHR₆ or NH-PG₁, wherein R₆ is alkyl, aminoalkyl or —C(O)-alkyl, and PG₁ is a suitable amine protecting group;

Y₃ is N or NH;

X₁ is N or CH;

X₂ is N or CH;

X₃ is N or CH;

R₂ is H, NH₂ or NHC(O)—R₇, wherein R₇ is alkyl, aryl, alkylaryl or aminoalkyl;

R₃ is present or absent and when present is —C(O)—, —C(O)NH—, —NH(O)C— or —N=N—; and R₄ is a substituted five or six-membered aryl or heteroaryl, wherein the substitution on the six-membered aryl is other than fluorine substitution.

In some embodiments, the nucleotide, nucleoside, oligonucleotide, polynucleotide or peptide nucleic acid wherein the structural moiety has the structure:

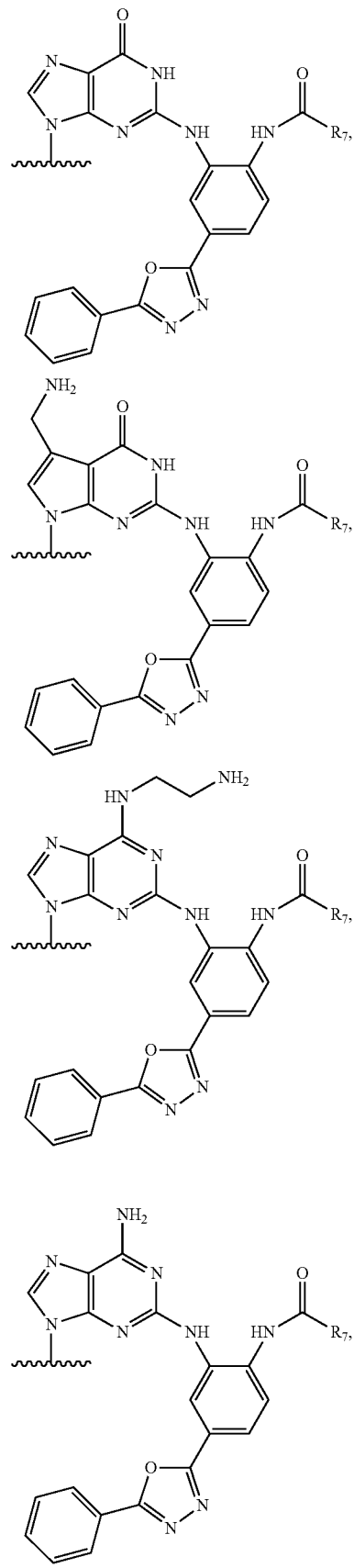

-continued
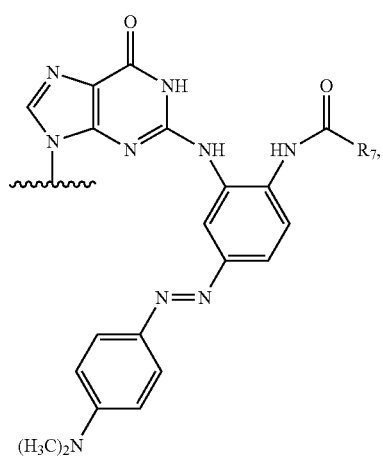
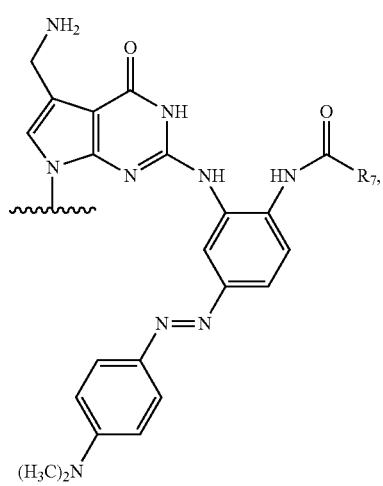
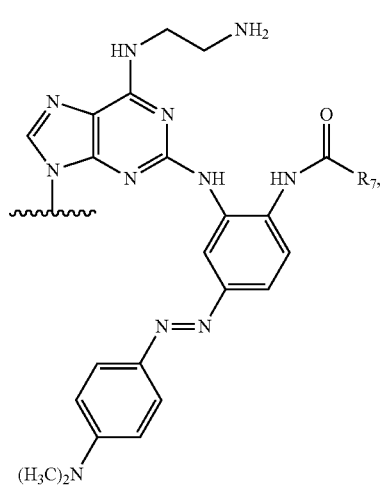
-continued
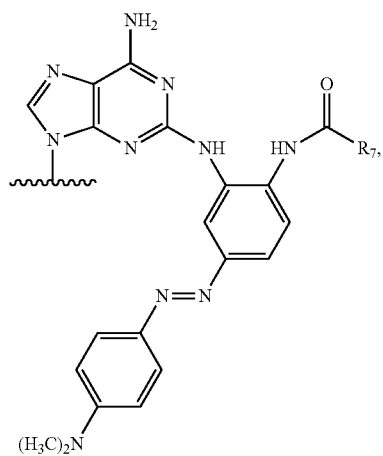
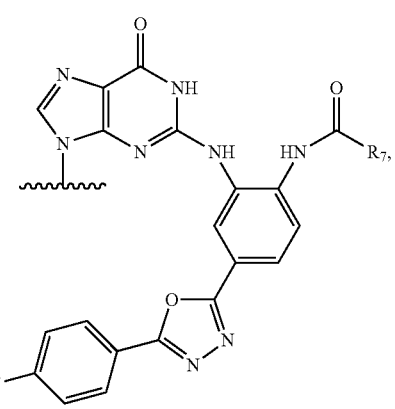
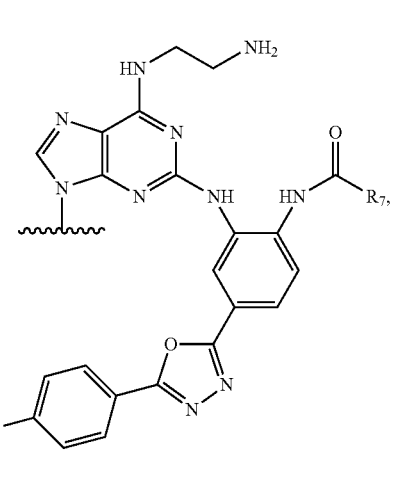

-continued
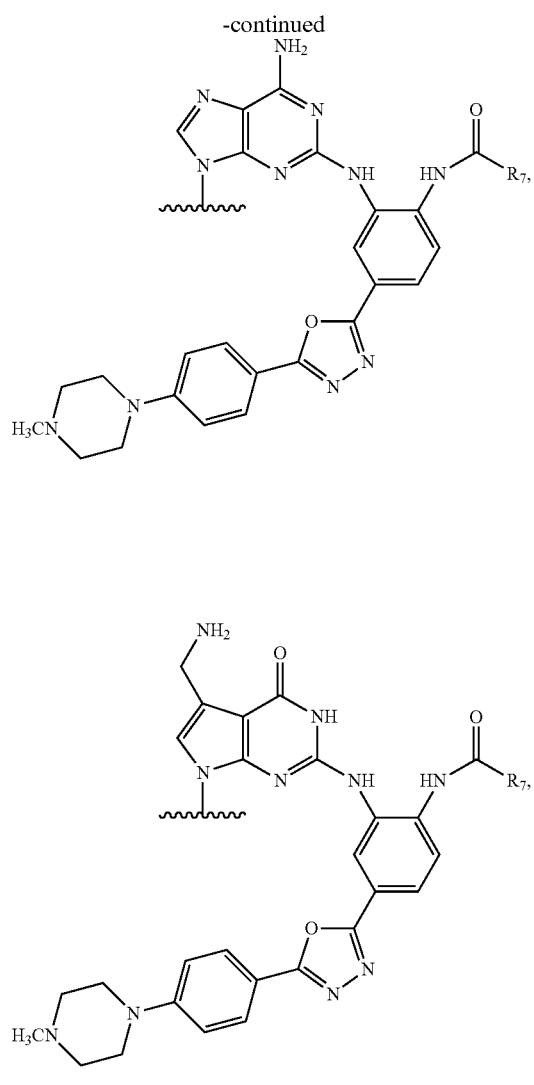
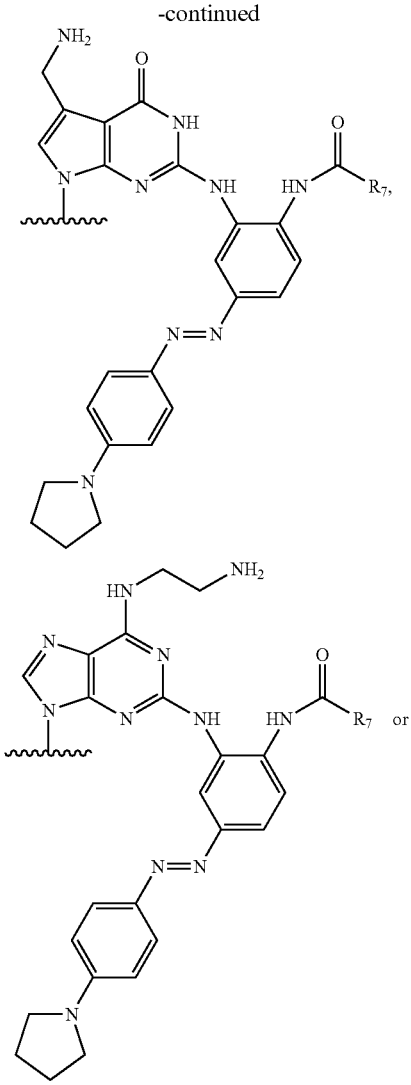
In some embodiments, the nucleotide, nucleoside, oligonucleotide, polynucleotide or peptide nucleic acid wherein the structural moiety has the structure:

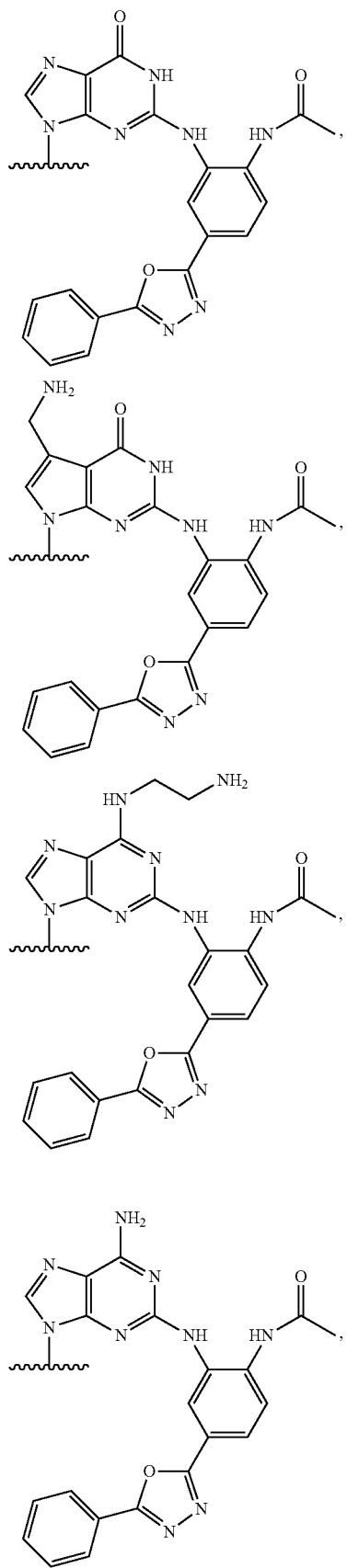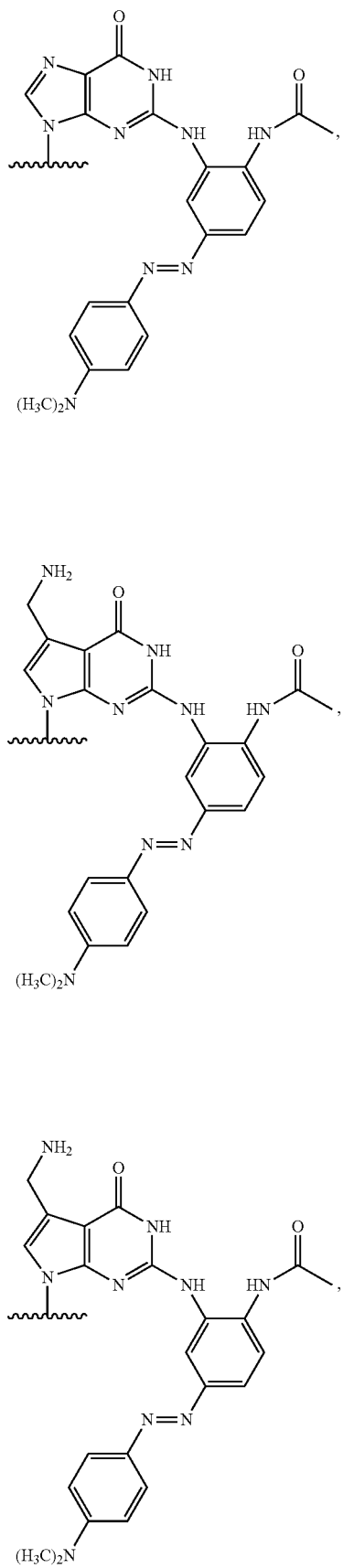

31
-continued
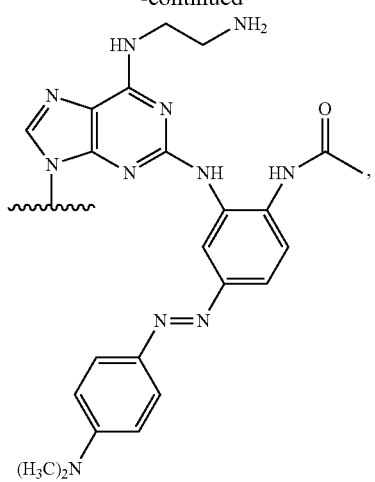
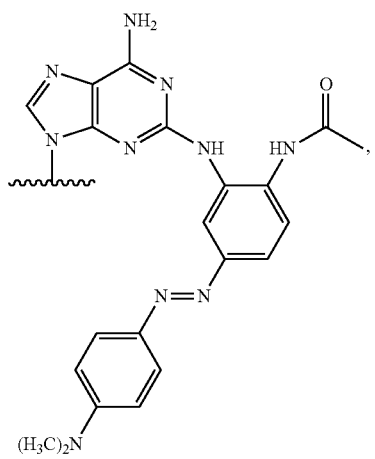
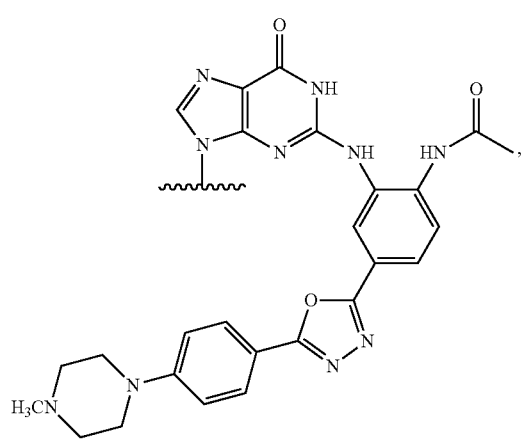
32
-continued
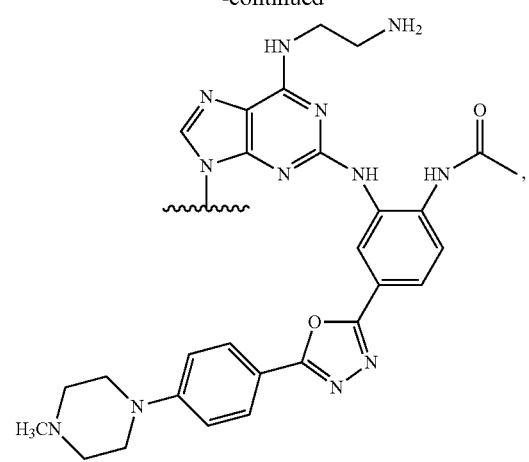
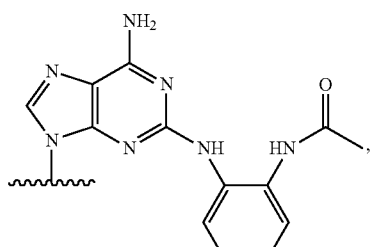
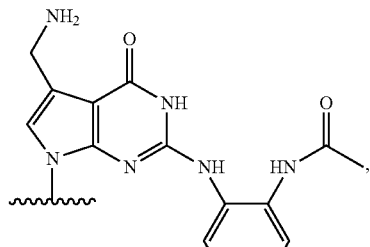

-continued
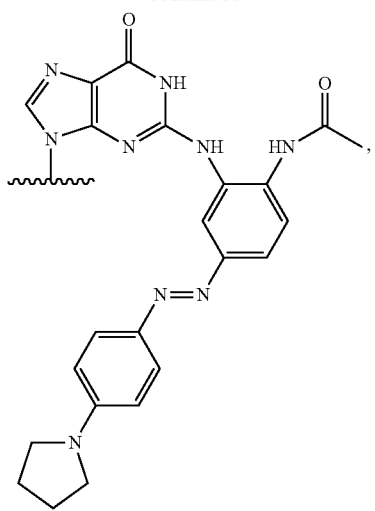
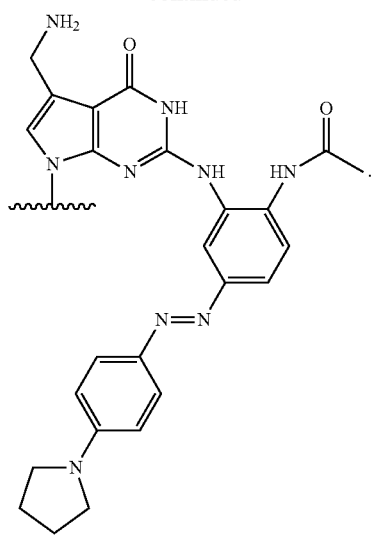
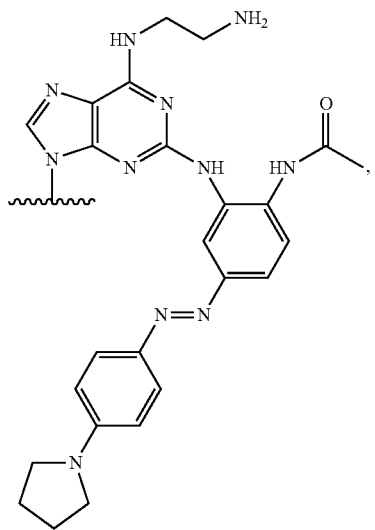
In some embodiments, the nucleotide, nucleoside, oligonucleotide, polynucleotide or peptide nucleic acid wherein the structural moiety has the structure:
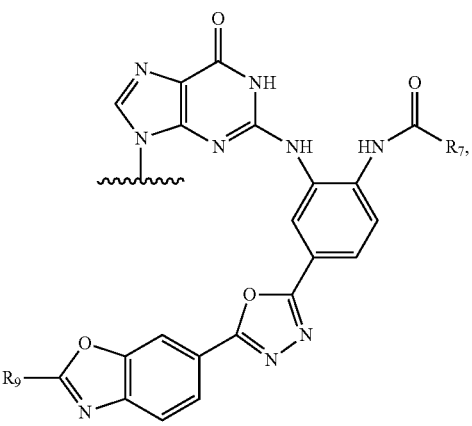
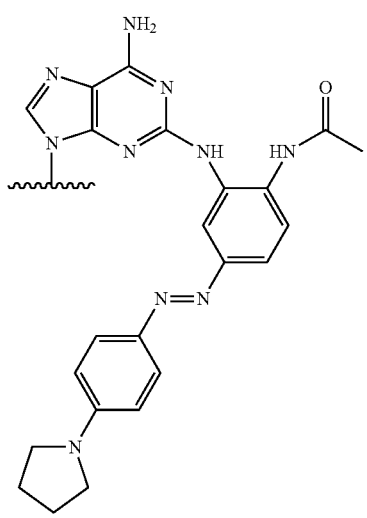
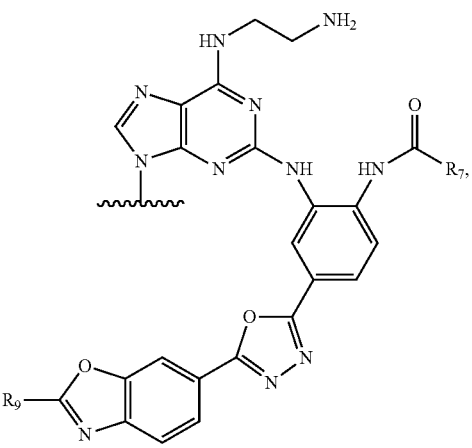
or

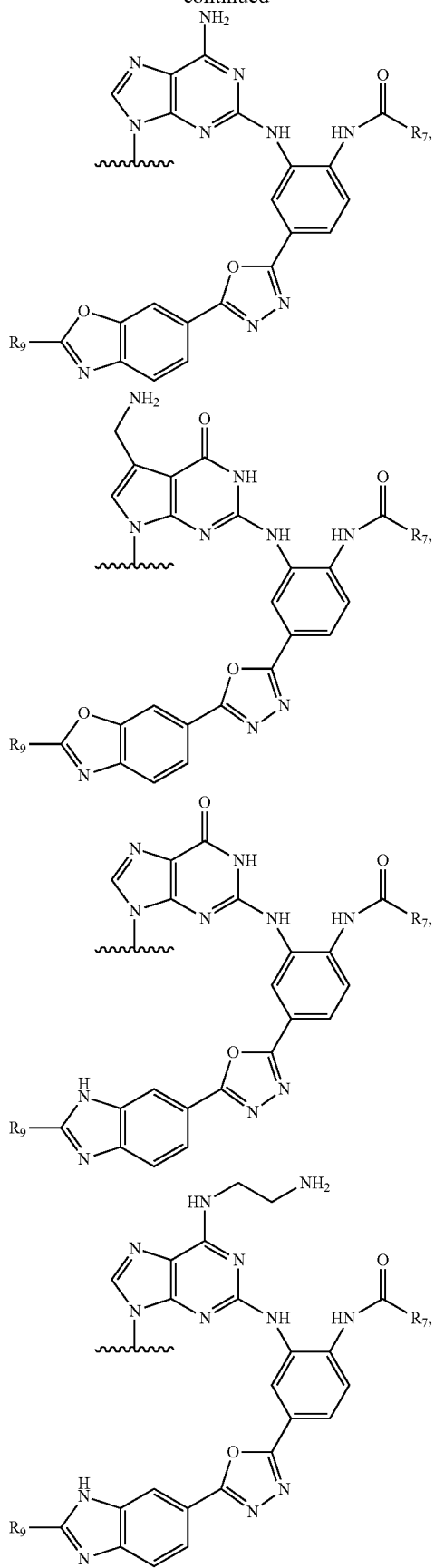
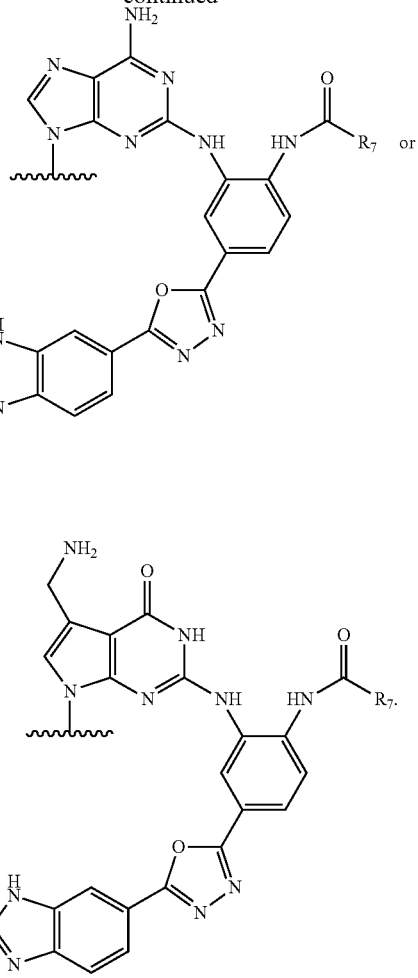
The present invention provides a process for making the compound having the structure:
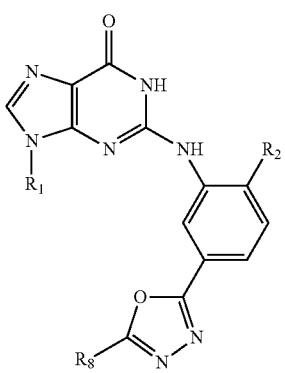
wherein
R₁ is a substituted tetrahydrofuran;
R₂ is NHC(O)—R₇,
wherein R₇ is alkyl, aryl, alkylaryl or aminoalkyl; and
R₈ is alkyl, alkenyl, alkynyl, aryl, substituted aryl, heteroaryl, substituted heteroaryl, heteroalkyl or heterocycloalkyl, comprising (a) reacting a compound having the structure:

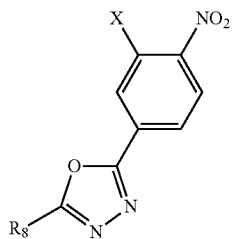

where X is a halogen, with a compound having the structure:

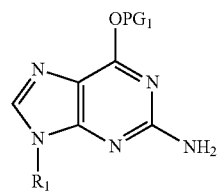

in the presence of a suitable cross coupling palladium catalyst in a first suitable solvent to produce a compound having the structure:

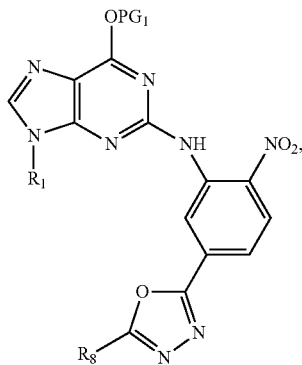

wherein

PG$_1$ is a suitable alcohol protecting group;

R$_1$ is a substituted tetrahydrofuran; and

R$_8$ is alkyl, alkenyl, alkynyl, aryl, substituted aryl, heteroaryl, substituted heteroaryl, heteroalkyl or heterocycloalkyl;

(b) reacting the product of step (a) with a suitable nitro reducing agent in a second suitable solvent to produce a free amine which is immediately reacted with a suitable anhydride or activate ester to produce the compound having the structure:

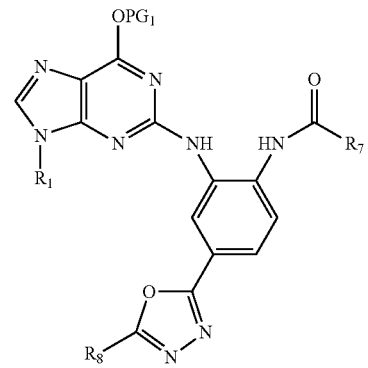

wherein

PG$_1$ is a suitable alcohol protecting group;

R$_1$ is a substituted tetrahydrofuran;

R$_7$ is alkyl, aryl, alkylaryl or aminoalkyl; and

R$_8$ is alkyl, alkenyl, alkynyl, aryl, substituted aryl, heteroaryl, substituted heteroaryl, heteroalkyl or heterocycloalkyl; and (c) reacting the product of step (b) with a suitable alcohol deprotecting agent to produce the compound.

The present invention provides a process for making the compound having the structure:

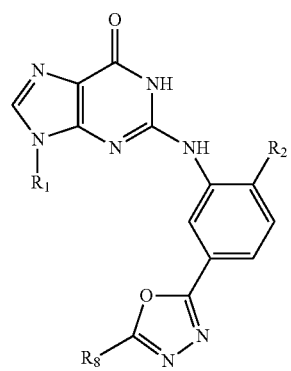

wherein

R$_1$ is a substituted tetrahydrofuran;

R$_2$ is NHC(O)—R$_7$, wherein R$_7$ is alkyl, aryl, alkylaryl or aminoalkyl; and R$_8$ is alkyl, alkenyl, alkynyl, aryl, substituted aryl, heteroaryl, substituted heteroaryl, heteroalkyl or heterocycloalkyl, comprising (a) reacting a compound having the structure:

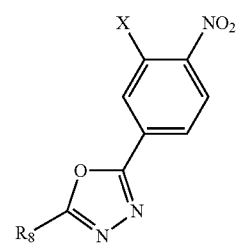

where X is a halogen, with a compound having the structure:

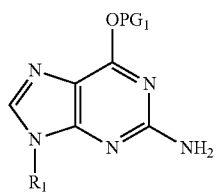

in the presence of a suitable cross coupling palladium catalyst in a first suitable solvent to produce a compound having the structure:

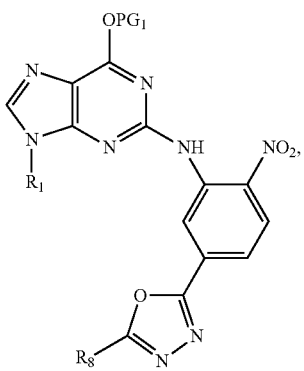

wherein
PG$_1$ is a suitable alcohol protecting group;
R$_1$ is a substituted tetrahydrofuran; and
R$_8$ is alkyl, alkenyl, alkynyl, aryl, substituted aryl, heteroaryl, substituted heteroaryl, heteroalkyl or heterocycloalkyl;

(b) reacting the product of step (a) with a suitable reducing and deprotecting agent in a second suitable solvent to simultaneously reduce the nitro group to a free amine and deprotect the alcohol to produce the compound having the structure:

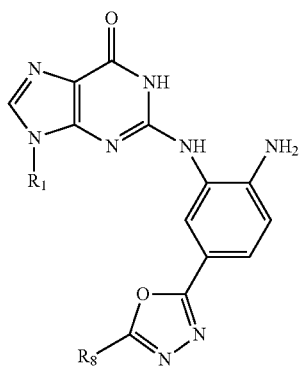

wherein
R$_1$ is a substituted tetrahydrofuran; and
R$_8$ is alkyl, alkenyl, alkynyl, aryl, substituted aryl, heteroaryl, substituted heteroaryl, heteroalkyl or heterocycloalkyl; and (c) reacting the product of step (b) with a suitable anhydride or activate ester in a third suitable solvent to produce the compound.

The present invention provides a process for making the compound having the structure:

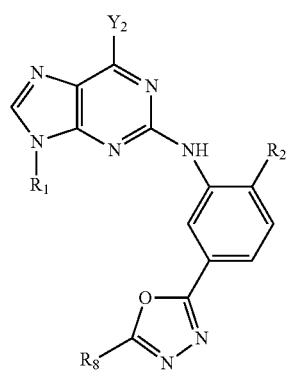

wherein
Y$_2$ is NHR$_6$,
wherein R$_6$ is alkyl, aminoalkyl or —C(O)-alkyl;
R$_1$ is a substituted tetrahydrofuran;
R$_2$ is NHC(O)—R$_7$,
wherein R$_7$ is alkyl, aryl, alkylaryl or aminoalkyl;
R$_8$ is alkyl, alkenyl, alkynyl, aryl, substituted aryl, heteroaryl, substituted heteroaryl, heteroalkyl or heterocycloalkyl, comprising (a) reacting a compound having the structure:

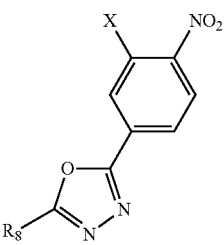

where X is a halogen, with a compound having the structure:

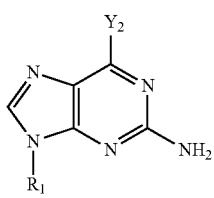

in the presence of a suitable cross coupling palladium catalyst in a first suitable solvent to produce a compound having the structure:

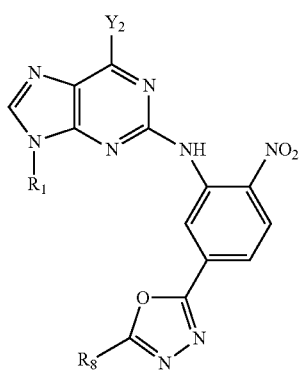

wherein
Y$_2$ is NHR$_6$,
wherein R$_6$ is alkyl, aminoalkyl or —C(O)-alkyl;
R$_1$ is a substituted tetrahydrofuran;
R$_2$ is NHC(O)—R$_7$,
wherein R$_7$ is alkyl, aryl, alkylaryl or aminoalkyl;
R$_8$ is alkyl, alkenyl, alkynyl, aryl, substituted aryl, heteroaryl, substituted heteroaryl, heteroalkyl or heterocycloalkyl; and
(b) reacting the product of step (a) with a suitable nitro reducing agent to produce a free amine which is immediately reacted with a suitable anhydride or activate ester to produce the compound.

Another version of the above process includes simultaneous reduction of the amino group and removal of PG$_1$ followed by the reaction of the amine obtained with suitable anhydride.

The present invention provides a process for making the compound having the structure:

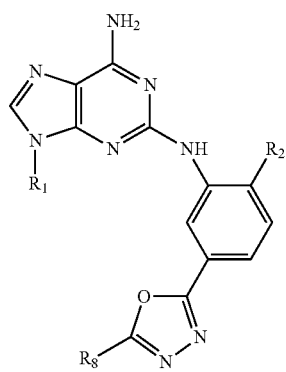

wherein
R$_1$ is a substituted tetrahydrofuran;
R$_2$ is NHC(O)—R$_7$,
wherein R$_7$ is alkyl, aryl, alkylaryl or aminoalkyl;
R$_8$ is alkyl, alkenyl, alkynyl, aryl, substituted aryl, heteroaryl, substituted heteroaryl, heteroalkyl or heterocycloalkyl, comprising (a) reacting a compound having the structure:

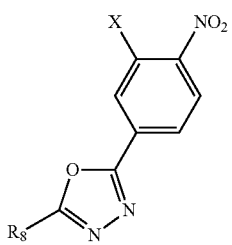

where X is a halogen, a compound having the structure:

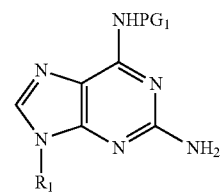

in the presence of a suitable cross coupling palladium catalyst in a first suitable solvent to produce a compound having the structure:

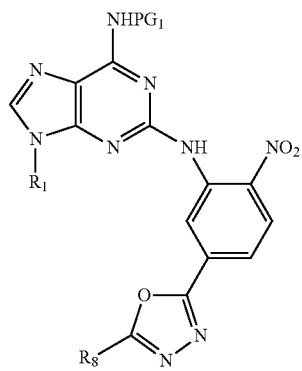

wherein
PG$_1$ is a suitable amine protecting group;
R$_1$ is a substituted tetrahydrofuran;
R$_2$ is NHC(O)—R$_7$,
wherein R$_1$ is alkyl, aryl, alkylaryl or aminoalkyl;
R$_8$ is alkyl, alkenyl, alkynyl, aryl, substituted aryl, heteroaryl, substituted heteroaryl, heteroalkyl or heterocycloalkyl;

(b) reacting the product of step (a) with a suitable nitro reducing agent in a second suitable solvent to produce a free amine which is immediately reacted with a suitable anhydride or activate ester to produce the compound.

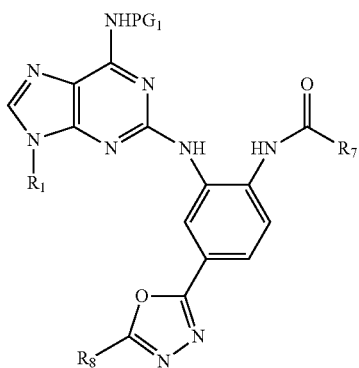

wherein
PG$_1$ is a suitable amine protecting group;
R$_1$ is a substituted tetrahydrofuran;
R$_7$ is alkyl, aryl, alkylaryl or aminoalkyl; and
R$_8$ is alkyl, alkenyl, alkynyl, aryl, substituted aryl, heteroaryl, substituted heteroaryl, heteroalkyl or heterocycloalkyl; and
(c) reacting the product of step (b) with a suitable amine deprotecting agent to produce the compound.

In some embodiments of the process, the nitro reducing agent is zinc.

In some embodiments of the process, the cross coupling palladium catalyst is formed by mixing Pd(OAc)$_2$ and OXPHOS ligand.

In some embodiments of the process, the suitable anhydride is acetic anhydride.

In some embodiments of the process, the deprotecting agent is ammonium formate in the presence of Pd on carbon.

In some embodiments of the process, R$_8$ has the structure:

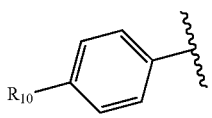

wherein R$_{10}$ is alkyl, aminoalkyl, aryl, substituted aryl, heteroaryl, substituted heteroaryl or heterocycloalkyl.

In some embodiments of the process, R$_8$ has the structure:

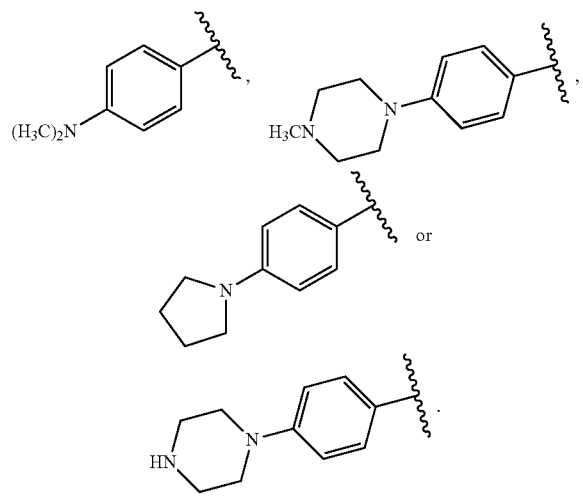

The present invention provides oligonucleotides or oligodeoxynucleotides with increased duplex stability.

The present invention also provides nucleoside monomers which are useful as intermediates in the synthesis of the oligonucleotides or oligodeoxynucleotides.

The present invention also provides nucleoside phosphoramidites monomers which are useful as intermediates in the synthesis of the oligonucleotides or oligodeoxynucleotides.

The compounds of the present invention are useful in the diagnostic, analytic and therapeutic fields, or as intermediates in the preparation of compounds useful in such fields.

The nucleoside monomers described herein are useful in preparing oligonucleotides for diagnostic or therapeutic use. The oligonucleotides are useful in therapeutic or diagnostic utilities where highly stable duplex structures are desired.

The structural stability of a nucleic acid duplex depends among other factors on the temperature. Stability of a duplex is therefore most often characterized by the stability of the duplex against heat-induced denaturation or thermal denaturation. Ultraviolet optical density of a nucleic acid solution depends on the secondary structure of a nucleic acid that is on the fact whether the nucleic acid is a duplex or a denatured random coil. In this way, duplex stability can be characterized by parameters obtained from plots of ultraviolet optical density versus temperature or from melting profiles of nucleic acid solutions. The results of our duplex stability experiments are shown in FIGS. 1-5.

The term "nucleotide," as used herein, generally refers to a nucleoside-5'-phosphate compound, or structural analog of a nucleoside-5'-phosphate that can have a modified base moiety (e.g., a substituted purine or pyrimidine base), a modified sugar (e.g., an O-alkylated sugar), and/or a modified polyphosphate moiety (e.g., a polyphosphate comprising a thio-phosphate, a methylene, and/or other bridges between phosphates).

The term "nucleotide analog," as used herein refers to a chemical compound that is structurally similar to a nucleoside-5'-phosphate. A nucleotide analog may have a modified base moiety, for example a substituted purine or pyrimidine base, a modified sugar such as an O-alkylated sugar, and/or a modified polyphosphate moiety, for example, a polyphosphate comprising a thiophosphate, a methylene, and/or other bridges between phosphates. It can have more than three phosphates in the polyphosphate chain, and it can be detectably tagged on any of the base, sugar or polyphosphate moieties.

The term "oligonucleotide," as used herein refers to an oligomer of nucleotide monomer units wherein the oligomer optionally includes non-nucleotide monomer units, and/or other chemical groups attached at internal and/or external positions of the oligomer. The oligonucleotide can be natural or synthetic and can include nucleosides with non-naturally-occurring (or modified) bases, sugar moieties, phosphodiester-analog linkages, and/or alternative monomer unit chiralities and isomeric structures (e.g., 5'-to-2' linkage, L-nucleosides, α-anomer nucleosides). Oligonucleotides generally include less than 30 monomer units.

The term "polynucleotide," as used herein refers to a polygomer of nucleotide monomer units wherein the poly optionally includes non-nucleotide monomer units, and/or other chemical groups attached at internal and/or external positions of the polygomer. The polynucleotide can be natural or synthetic and can include nucleosides with non-naturally-occurring (or modified) bases, sugar moieties, phosphodiester-analog linkages, and/or alternative monomer unit chiralities and isomeric structures (e.g., 5'-to-2' linkage, L-nucleosides, α-anomer nucleosides). Polynucleotides generally include greater than 30 monomer units.

The term "peptide nucleic acid," as used herein refers to a oligonucleotide or polynucleotide where the nucleobase is retained but the ribose phosphodiester backbone is replaced by a pseudo-peptide to which the nucleobases are linked.

The term "nucleic acid," as used herein, generally refers to a molecule comprising one or more nucleotide subunits. A nucleotide may include one or more subunits selected from adenine (A), cytosine (C), guanine (G), thymine (T) and uracil (U). In some examples, a nucleic acid is deoxyribonucleic acid (DNA) or ribonucleic acid (RNA), or derivatives thereof. A nucleic acid may be single-stranded or double stranded.

One of ordinary skill in the art would readily understand that nucleoside phosphoramidites are used to synthesize oligonucleotides. The term "phosphoramidite group," as used herein, generally refers to a group containing a trivalent phosphorus atom attached to the dialkylamino group. Phosphoramidite group serves as an activated precursor of the phosphate group during the synthesis of oligonucleotides. Nucleoside phosphoramidites, which contain phosphoramidite group at the 3' hydroxyl group can be prepared by methods known in the art.

To prevent undesired side reactions when synthesizing oligonucleotides, all other functional groups present in nucleosides must be protected by suitable protecting groups. The 5' and 2' hydroxyl groups must be protected with suitable hydroxyl protecting groups. Any reactive functional groups on the nucleobase, i.e. exocyclic amine, must be protected with suitable hydroxyl protecting groups.

$PG_1$ includes, but is not limited to, amide protecting groups including benzoyl, isobutyryl, phenoxyacetyl, and also includes any other protecting groups used in phosphoramidite or H-phosphonate oligonucleotide synthesis protocols.

$PG_2$ includes, but is not limited to, trityl, monomethoxy trityl (MMT), dimethoxytrityl (DMT), acetyl, benzoyl, isobutyl and 5'-O-(α-methyl-6-nitropiperonyloxycarbonyl) (MeNPOC), and also includes any other 5' hydroxyl protecting groups used in phosphoramidite or H-phosphonate oligonucleotide synthesis protocols.

$PG_3$ includes, but is not limited to, tert-butyldimethylsilyl (TBDMS or TBS), triisopropylsilyloxymethyl (TOM), bis(2 acetoxyethoxy)methyl (ACE) or thiomorpholine-4-carbothioate (TC), and also includes any other 2' hydroxyl protecting groups used in phosphoramidite or H-phosphonate oligonucleotide synthesis protocols.

$PG_4$ includes, but is not limited to, 2-cyanoethyl N, N-diisopropylphosphoramidite, and also includes any other 2' hydroxyl phosphoramidite or H-phosphonate groups used in phosphoramidite or H-phosphonate oligonucleotide synthesis protocols.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon or nitrogen-nitrogen double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on, or any length therein. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_4$-$C_{12}$ alkenyl and so on or any length therein.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl, $C_3$-$C_{12}$ alkynyl, $C_4$-$C_{12}$ alkynyl and so on or any length therein.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "aminoalkyl" includes both branched and straight-chain saturated aliphatic hydrocarbon groups having at least N heteroatom within the chain or branch or a terminal —$NH_2$ group.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "heterocycloalkyl" is intended to mean a 5- to 10-membered nonaromatic ring containing from 1 to 4 heteroatoms selected from the group consisting of O, N and S, and includes bicyclic groups. "Heterocycl" includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl, 4-mehtylpiperazinyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethyl-phenylmethyl), 1-phenylethyl, 2-phenylethyl, 3-phenylpropyl, 2-phenylpropyl and the like.

The alkyl, aminoalkyl, alkenyl, alkynyl, aryl, alkylaryl, heteroaryl and heterocycloalkyl substituents may be substituted or unsubstituted, unless specifically defined otherwise. In the compounds of the present invention, the alkyl, aminoalkyl, alkenyl, alkynyl, aryl, alkylaryl, heteroaryl and heterocycloalkyl groups can be further substituted by replacing one or more hydrogen atoms with alternative non-hydrogen groups. These include, but are not limited to, halo, hydroxy, mercapto, amino, carboxy, cyano and carbamoyl, dialkylamino, etc.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention. This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

The precursor diphenyl oxodiazole bromide can be easily prepared and its coupling to the nucleosides is achieved by means of Pd-catalyzed Buchwald-Hartwig amination.

Example 1. Synthesis of PDZ-dG

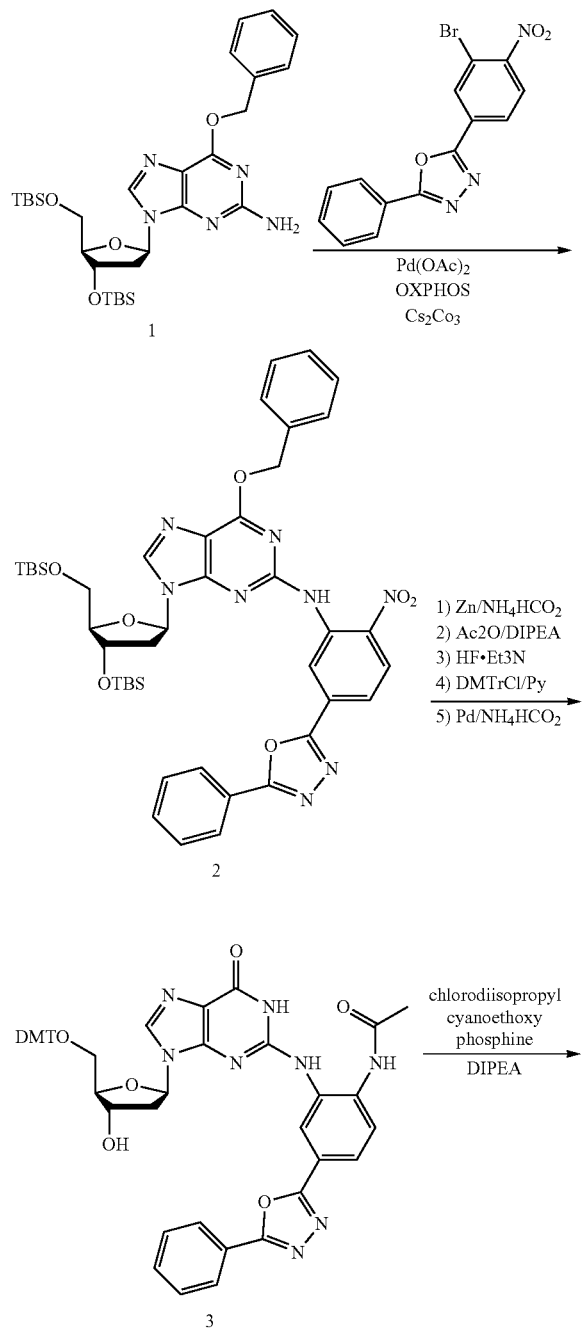

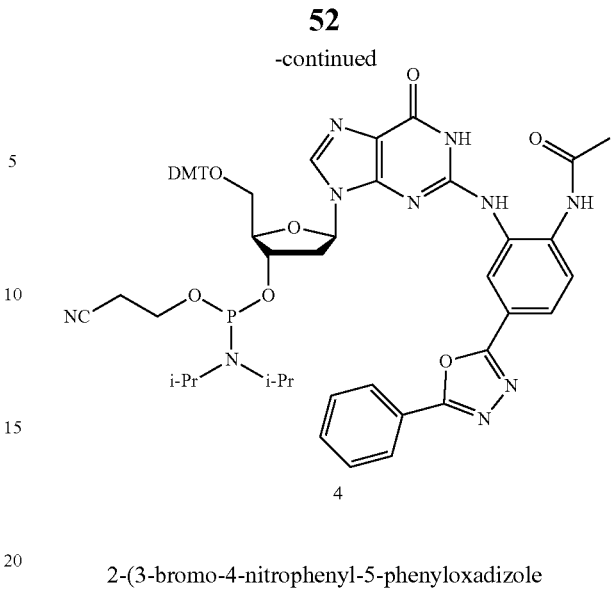

2-(3-bromo-4-nitrophenyl-5-phenyloxadizole 2.46 g 3-bromo-4-nitrobenzoic acid (10 mmol) and 1.36 g of benzoyl hydrazide (10 mmol) and 3.5 mL diisopropylethylamime (20 mmol) we mixed in 100 mL of anhydrous acetonitrile, and 4.54 g of HBTU (12 mmol) were added. The mixture was briefly heated until a full dissolution of all solids and stirred at room temperature overnight. 5.2 mL of diisopropylethylamine were added followed by 6 g (30 mmol) of toluenesulfonyl chloride. The mixture was briefly heated to 70° until all solids dissolved, and after that it was stirred for additional 6 hours. 200 mL of dichloromethane was added followed by 300 mL of 10% aqueous ammonia. The organic layer was separated, washed with water, dried with sodium sulfate, and evaporated. The solid was purified by flash chromatorgaphy. Yield 3.1 g. $^1$H-NMR (CDCl$_3$, TMS): 8.55 (d, 1H), 8.27 (dd, 1H), 9.19 (d, 2H), 8.04 (d, 1H), 7.64 (m, 1H) 7.6 (m, 2H).

6-(benzyloxy)-9-{4-[(tert-butyldimethylsilyl)oxy)-5-{[(tert-butyldimethylsilyl)oxy]methyl}oxolan-2-yl}-N-[2-nitro-5-(5-phenyl-1,3,4-oxadiazol-2-yl)phenyl]purin-2-amine (Compound 2)

1.23 g (2.1 mmol) of O$^6$-benzyl-3',5'-bis(tert-butyldimethylsilyl)-2'-deoxyguanozine, 937 mg (2.7 mmol) of 2-(3-bromo-4-nitrophenyl_-5-phenyloxadizole, 1.2 g (3.7 mmol) of cesium carbonate, 121 mg (0.21 mmol) of OXPHOS, and 22.4 (0.1 mmol) of palladium (II) acetate were placed to the round bottom flask with a stirring bar. The flask was sealed and purged with nitrogen, and 10 mL of dry toluene were injected with a syringe. The reaction mixture was stirred at 90° C. for 2 hr, cooled to the room temperature, diluted with 100 mL of dichloromethane, filtered through Celite, and evaporated. The residue was recrystallized from methanol to yield 1.5 g (1.76 mmol) of the final product as a orange-red powder. $^1$H-NMR (CDCl$_3$, TMS): 10.56 (s, 1H). 10.01 (s, 1H), 8.45 (d, 1H), 8.19 (s, 1H), 8.15 (d, 2H), 7.78 (d, 1H), 7.6-7.5 (m, 5H) 7.37-7.31 (m, 3H), 6.50 (t, 1H), 5.77 (m, 2H), 4.64 (m, 1H), 3.96 (m, 1H), 3.88 (m, 1H), 3.79 (m, 1H), 2.66 (m, 1H), 2.51 (m, 1H), 0.92 (s, 9H), 8.87 (s, 9H), 0.1 (s, 3H) 0.88 (s, 3H), 0.077 (s, 6H).

N-(2-([9-(5-[bis(4-methoxyphenyl) (phenyl) methoxy]methyl)-4-hydroxyoxolan-2-yl)-6-oxo-1H-purin-2-yl]amino)-4-(5-phenyl-1,3,4-oxadiazol-2-yl) phenyl)acetamide (Compound 3)

1.2 g (1.41 mmol) of compound 2 were dissolved in 30 mL methanol/THF (2:1). Ammonium formate (3 g) and zinc powder (400 mg) were added, and the mixture was refluxed for 5 hours. The reaction was allowed to cool down to the room temperature, 100 mL of dichloromethane were added, and the organic phase was extracted with 10% aqueous sodium citrate. The organic phase was separated, filtered through Celite, evaporated, and dried at 0.1 mtorr. The residue was dissolved in 20 mL of dry dichloromethane, and 3 ml of acetic anhydride/4 mL diisopropylethylamine were added. After 4 hours, the mixture was diluted with 100 mL of dichloromethane and extracted with 10% sodium carbonate (3×200 mL). The organic phase was separated, dried with sodium sulfate, and evaporated. The oil obtained was dissolved in 3 mL of dry DMF and placed into the 50 mL plastic centrifuge tube. 1 mL of triethylamine was added followed by 1.2 mL of triethylamine trihydrofluoride. The mixture was incubated at 50° C. for 1 hr, and 45 mL of water were added. The resulting precipitate was collected by centrifugation and dried in vacuo. The solid obtained was dissolved in 10 mL of pyridine and evaporated, dissolved in dry pyridine, and evaporated again. After three rounds of co-evaporation, the residue was dissolved in 10 mL of anhydrous pyridine, and 544 mg (1.6 mmol) of dimethoxytritylchloride were added. The consumption of the starting nucleoside was monitored by TLC (dichloromethane-ethanol 10:1). When the starting material is fully consumed (usually, in 1 hr), 2 mL of methanol were added to the reaction mixture, followed by 100 ml of dichloromethane. The solution was washed with 10% sodium carbonate (4×100 mL), separated, dried with sodium sulfate, evaporated in vacuo, and co-evaporated with toluene (3×10 mL). The solid obtained was dissolved in 3 mL of dichloromethane and flash chromatographed (step gradient of methanol in dichloromethane, 0→5%, in the presence of 0.05% of triethylamine). The main fraction, which contained the protected nucleoside, was collected and evaporated in vacuo.

The nucleoside obtained was dissolved in 4 mL of THF, 20 mL of methanol were added, followed by 2 g of ammonium formate and 50 mg of Pd/C (10%). The mixture was refluxed until a full consumption of the starting material (about 2 hrs), allowed to cool to room temperature, diluted with 150 mL dichloromethane and extracted with sodium bicarbonate (2×100 mL) and water (2×100 mL), dried with anhydrous sodium sulfate, and evaporated. The product was obtained as a colorless amorphous solid. $^1$H-NMR (DMSO, TMS), 8.82 (s, 1H), 8.14 (d, 2H), 7.92 (s, 1H), 7.82 (d, 1H), 7.80 (br s, 1H), 7.64 (m, 3H), 7.21 (d, 2H), 7.15 (m, 3H), 7.08 (m, 5H) 6.75 (d, 2H), 6.71 (d, 2H), 6.20 (t, 1H), 4.32 (m, 1H), 3.68 (s, 3H), 3.67 (s, 3H), 3.43 (m, 1H), 3.05 (m, 2H), 2.62 (m, 1H), 2.51 (s, 3H), 2.27 (m, 1H), 2.25 (m, 1H).

N-(2-{[9-(5-{[bis(4-methoxyphenyl) (phenyl) methoxy methyl})-4-[{(2-cyanoethoxy) (diisopropylamino)phosphanyl]oxy}oxolan-2-yl)-6-oxo-1H-purin-2-yl]amino}-4-(5-phenyl-1,3,4-oxadiazol-2-yl) phenyl)acetamide (Compound 4)

Nucleoside 3 (810 mg, 0.95 mmol) was dissolved in 5 mL of anhydrous THF, and 0.4 mL of diisopropylamine was added. The flask was flushed with nitrogen, and 300 mg of cyanoethoxydiisopropylamino chlorophosphine were added dropwise. The mixture was standing for 2 hours, and starting material was fully consumed judging by TCL (dichloromethane-methanol 10:1). The reaction was diluted with 100 mL of dichloromethate, washed with 10% sodium carbonate (100 mL), the organic phase was separated, dried with sodium sulfate, evaporated and co-evaporated with anhydrous acetonitrile (3×10 mL). The product obtained is the phosphoramidite 4 that can be used for the oligonucleotide synthesis without further purification. If necessary, the amidite 4 can be purified by means of flash chromatography (silica, dichloromethane-methanol-triethylamine 100:5:1).

Example 2. Synthesis of PDZ-dA

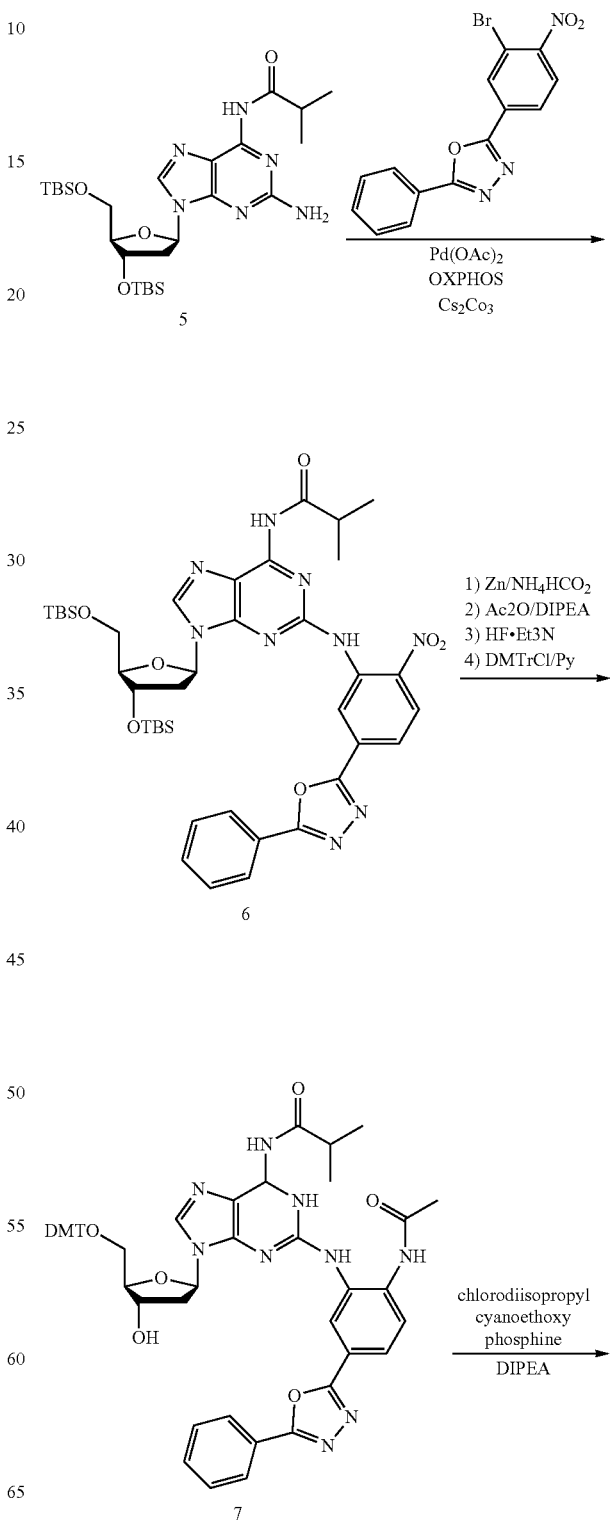

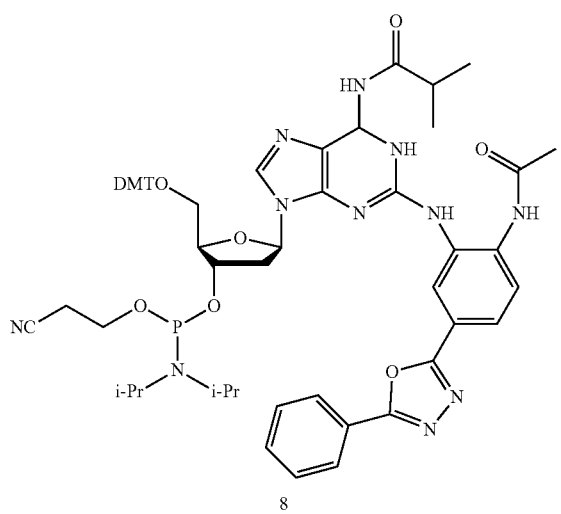

8

Synthesis of the amidite 8 (PDZ-dA) was performed as described in the example 1, except the Pd/C hydrogenation step was omitted.

Example 3. Synthesis of the MMPizPDZ-dG Amidite

A. Synthesis of 2-(3-chloro-4-nitrophenyl-5-(4-(4-methylpiperazine-1-yl)phenyloxadizole (Compound 11)

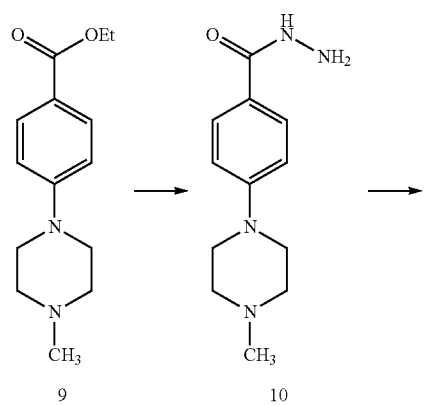

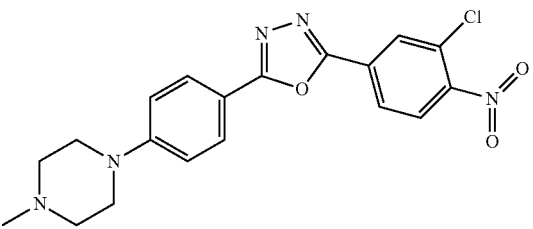

11

4-(4-methylpiperazine-1-yl)benzoyl hydrazide (Compound 10)

To 9.6 g of ethyl 4-(4-methylpiperazin-1-yl)benzoate (9) in 100 mL of methoxyethanol 10 mL of hydrazine hydrate were added, and the resulting solution was refluxed until TLC shows disappearance of the starting ester. The reaction mixture was evaporated in vacuo, re-evaporated with n-butanol three times, and crystallized from butanol, and dried over $P_2O_5$. 9.1 g of the hydrazide (10) were obtained as a white powder. $^1$H-NMR (CDCl$_3$, TMS): 2.37 (s, 3H), 2.57 (m, 4H), 3.33 (m, 4H), 4.09 (br s, 2H), 6.91 (d, 2H), 7.37 (s, 1H), 7.68 (d, 2H). $^{13}$C-NMR (CDCl$_3$, TMS): 46.16, 47.69, 54.81, 114.27, 122.13, 128.27, 153.54, 168.51.

2-(3-chloro-4-nitrophenyl-5-(4-(4-methylpiperazine-1-yl)phenyloxadizole (Compound 11)

2.34 g (10 mmol) of hydrazide (10) and 2.01 g (10 mmol) of 3-chloro-4nitrobenzoic acid were mixed in 60 mL of anhydrous acetonitrile. 2 mL of DIPEA were added, and the mixture was heated briefly until all solids dissolve. 4 g (1.05 mmol) of HBTU were added, and the mixture was stirred for one hour. A copious precipitate formed. To the reaction mixture, 5 mL of DIPEA were added followed by 6 g (30 mmol) of tosyl chloride. The mixture was briefly heated to boiling, the precipitate dissolved, and a new precipitated formed immediately after that. The reaction was standing overnight at room temperature, the precipitate was collected by filtartion, washed with methanol and dried in vacuo. 3.5 g 8.77 mmol) of the compound 11 were obtained. $^1$H-NMR (CDCl$_3$, TMS): 2.40 (s, 3H), 2.62 (br s, 4H), 3.43 (br s, 4H), 7.02 (d, 2H), 8.03 (d, 2H), 8.05 (d, 1H), 8.18 (d, 1H), 8.33 (s, 1H). $^{13}$C-NMR (CDCl$_3$, TMS): 45.44, 46.52, 54.27, 112.08, 114.83, 126.72, 126.80, 127.32, 128.84, 129.51, 149.12, 153.48, 161.34, 165.81.

B. Synthesis of N-(2-{[9-(5-{[bis(4-methoxyphenyl)(phenyl)methoxy]methyl}-4-([(2-cyanoethoxy)(diisopropylamino)phosphanyl oxy)oxolan-2-yl)-6-oxo-1H-purin-2-yl]amino}-4-(5-(4-(4-methylpiperazine-1-yl)phenyl-1,3,4-oxadiazol-2-yl)phenyl) acetamide (Compound 16)
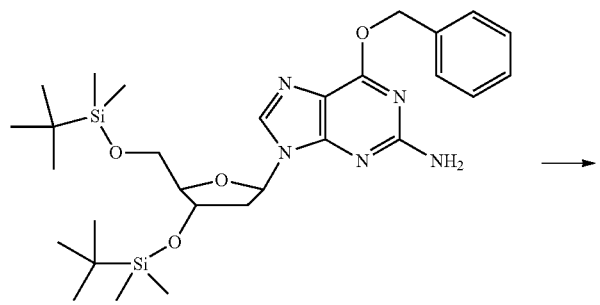
5
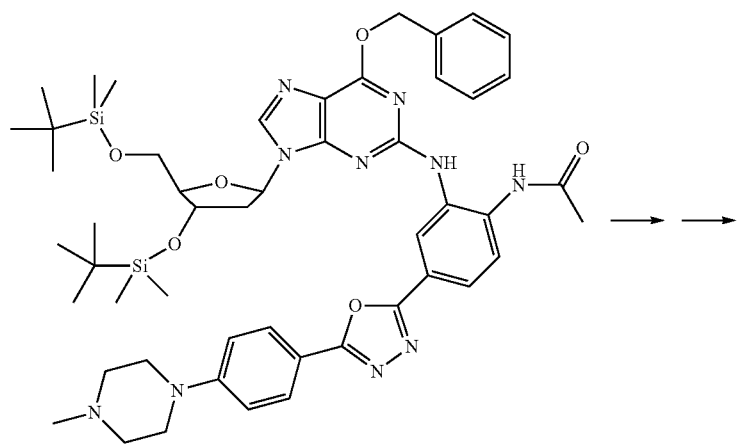
12
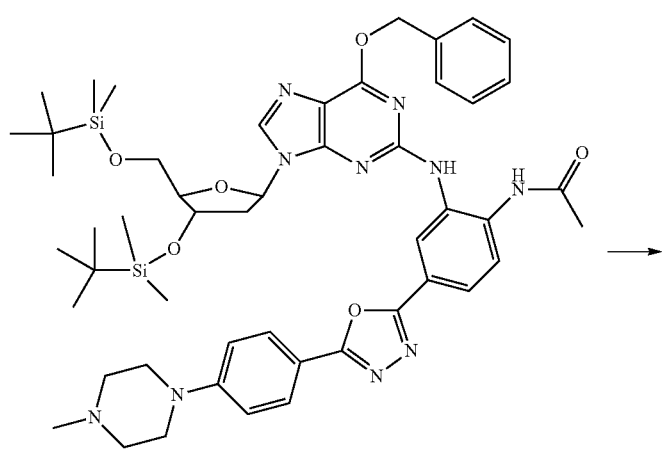
13

-continued
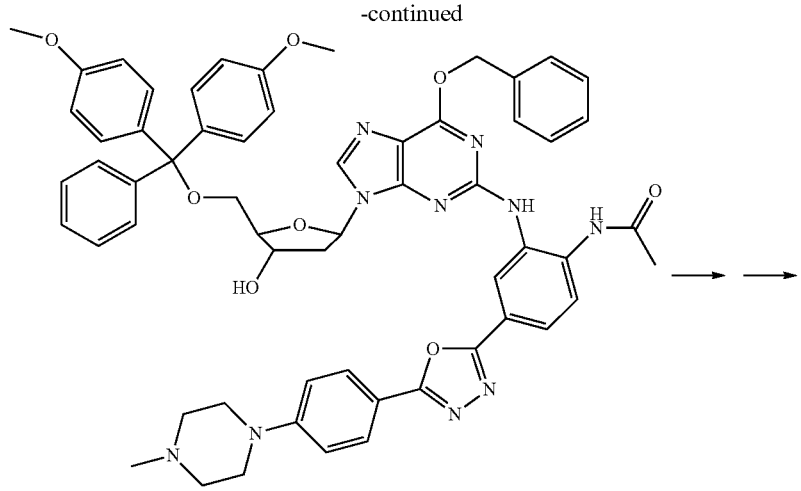
14
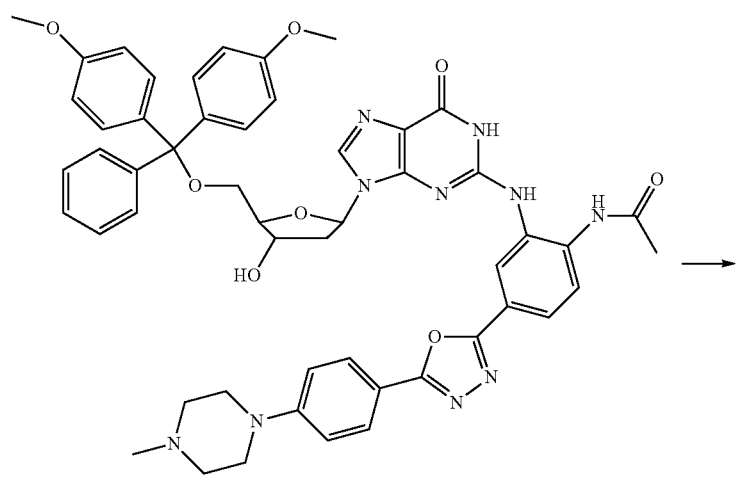
15
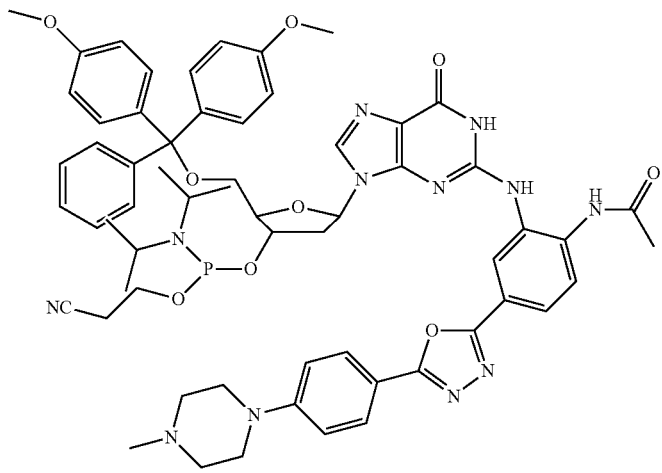
16

6-(benzyloxy)-9-(4-[(tert-butyldimethylsilyl)oxy]-5-([(tert-butyldimethylsilyl)oxy]methyl)oxolan-2-yl)-N-[2-nitro-5-(5-(4-(4-mehylpiperazin-1-yl)phenyl-1,3,4-oxadiazol-2-yl)phenyl]purin-2-amine (Compound 12)

1.7 g (2.9 mmol) of $O^6$-benzyl-3',5'-bis(tert-butyldimethylsilyl)-2'-deoxyguanozine, 1.16 g (2.9 mmol) of 2-(3-chloro-4-nitrophenyl-5-(4-(4-methylpiperazine-1-yl)phenyloxadizole, 0.975 g (3 mmol) of cesium carbonate, 119 mg (0.21 mmol) of OXPHOS, and 22.4 (0.1 mmol) of palladium (II) acetate were placed into the round bottom flask with a stirring bar. The flask was sealed and purged with nitrogen, and 10 mL of dry toluene were injected with a syringe. The reaction mixture was stirred at 100° C. for 3 hr, cooled to the room temperature, diluted with 100 mL of dichloromethane, filtered through Celite, and evaporated. The residue was purified using flash chromatography on silica (methylene chloride→5% methanol in methylene chloride). The final product was obtained as a red solid (2.07 g 2.2 mmol). $^1$H-NMR (CDCl$_3$, TMS): 0.08 (s, 12H), 0.87 (s, 9H), 0.90 (s, 9H), 2.46 (s, 3H), 2.71 (m, 4H), 3.40 (m, 4H), 3.80 (s, 1H), 3.86 (m, 1H), 3.96 (m, 1H), 4.62 (m, 1H), 5.74 (m, 2H), 6.47 (t, 1H), 6.91 (d, 2H), 7.29 (t, 1H), 7.33 (t, 2H), 7.55 (d, 2H), 7.72 (d, 1H), 7.95 (d, 2H), 8.19 (s, 1H), 8.39 (d, 1H), 9.92 (s, LH), 10.56 (s, 1H). $^{13}$C-NMR (CDCl$_3$, TMS): −5.46, −5.39, −4.85, −4.68, 17.94, 18.43, 18.47, 25.72, 25.97, 41.38, 46.14, 47.30, 47.39, 54.71, 54.73, 58.26, 62.51, 69.07, 71.32, 84.46, 87.67, 112.33, 112.83, 114.42, 114.49, 117.68, 118.11, 118.63, 125.46, 126.43, 127.14, 128.09, 128.18, 128.42, 128.45, 128.48, 128.60, 128.76, 129.63, 130.11, 135.84, 135.92, 137.93, 139.96, 148.81, 152.44, 153.39, 153.54, 160.56, 160.92, 162.44, 165.74.

N-(2-[9-(5-{[bis(4-methoxyphenyl) (phenyl) methoxy]methyl)-4-hydroxyoxolan-2-yl)-6-oxo-1H-purin-2-yl]amino)-4-(5-[4-(4-methylpiperazin-1-yl)phenyl]-1,3,4-oxadiazol-2-yl}phenyl)acetamide (Compound 15)

1.28 g (1.35 mmol) of compound 12 were dissolved in 30 mL methanol/THF (2:1). Ammonium formate (3.5 g) and zinc powder (400 mg) were added, and the mixture was refluxed for 3 hours. The reaction was allowed to cool down to the room temperature, 100 mL of dichloromethane were added, and the organic phase was extracted with 10% aqueous sodium citrate. The organic phase was separated, filtered through Celite, evaporated, and dried at 0.1 mtorr. The residue was dissolved in 20 mL of dry dichloromethane, and 3 ml of acetic anhydride/4 mL diisopropylethylamine were added. After 6 hours, the mixture was diluted with 100 mL of dichloromethane and extracted with 10% sodium carbonate (3×200 mL). The organic phase was separated, dried with sodium sulfate, and evaporated. The oil obtained was dissolved in 3 mL of dry DMF and placed into the 50 mL plastic centrifuge tube. 1 mL of triethylamine was added followed by 1.2 mL of triethylamine trihydrofluoride. The mixture was incubated at 50° C. for 1 hr, and 45 mL of water were added. The resulting precipitate was collected by centrifugation and dried in vacuo. The solid obtained was dissolved in 10 mL of pyridine and evaporated, dissolved in dry pyridine, and evaporated again. After three rounds of co-evaporation, the residue was dissolved in 10 mL of anhydrous pyridine, and 620 mg of dimethoxytritylchloride (DMT-Cl) were added. The consumption of the starting nucleoside was monitored by TLC (dichloromethane-ethanol 10:1). If the starting material is not fully consumed in 1 hr, additional amount of DMT-Cl (ca 100 mg) is added, and the reaction is monitored by TLC. When the starting nucleoside is fully consumed, 2 mL of methanol were added to the reaction mixture, followed by 100 ml of dichloromethane. The solution was washed with 10% sodium carbonate (4×100 mL), separated, dried with sodium sulfate, evaporated in vacuo, and co-evaporated with toluene (3×10 mL). The solid obtained was dissolved in 3 mL of dichloromethane and flash chromatographed (step gradient of methanol in dichloromethane, 0→5%, in the presence of 0.05% of triethylamine). The main fraction, which contained the protected nucleoside, was collected and evaporated in vacuo.

The nucleoside obtained was dissolved in 4 mL of THF, 20 mL of methanol were added, followed by 2 g of ammonium formate and 50 mg of Pd/C (10%). The mixture was refluxed until a full consumption of the starting material (about 2 hrs), allowed to cool to room temperature, diluted with 150 mL dichloromethane and extracted with sodium bicarbonate (2×100 mL) and water (2×100 mL), dried with anhydrous sodium sulfate, and evaporated. The product was obtained as a colorless amorphous solid.

N-(2-{[9-(5-{[bis(4-methoxyphenyl) (phenyl)methoxy]methyl}-4-{[(2-cyanoethoxy) (diisopropylamino)phosphanyl]oxy}oxolan-2-yl)-6-oxo-1H-purin-2-yl]amino}-4-(5-(4-(4-methylpiperazine-1-yl)phenyl-1,3,4-oxadiazol-2-yl)phenyl)acetamide (Compound 16)

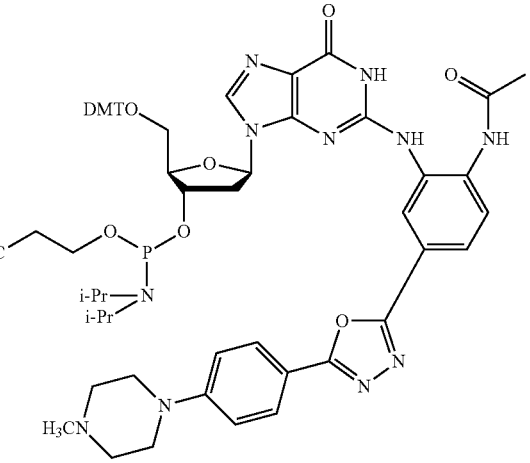

Nucleoside 15 (1.180 g, 1.25 mmol) was dissolved in 5 mL of anhydrous THF, and 0.5 mL of diisopropylamine was added. The flask was flushed with nitrogen, and 390 uL of cyanoethoxydiisopropylamino chlorophosphine were added dropwise. The mixture was standing for 2 hours, and starting material was fully consumed judging by TCL (dichloromethane-methanol 10:1). The reaction was diluted with 100 mL of dichloromethane, washed with 10% sodium carbonate (100 mL), the organic phase was separated, dried with sodium sulfate, evaporated and co-evaporated with anhydrous acetonitrile (3×10 mL). The product obtained is the phosphoramidite 16 that can be used for the oligonucleotide synthesis without further purification. If necessary, the amidite 16 can be purified by means of flash chromatography (silica, dichloromethane-methanol-triethylamine 100:5:1). $^{13}$C-NMR (CDCl$_3$, TMS): 13.54, 19.57, 20.01, 20.05, 20.24, 20.28, 22.61, 24.06, 24.35, 24.41, 24.45, 24.50, 43.08, 43.16, 43.23, 46.14, 47.45, 53.45, 54.71, 55.20, 55.22, 58.13, 58.23, 61.41, 84.61, 85.61, 85.74, 86.60, 113.17, 113.60, 114.57, 117.56, 117.86, 121.99, 127.05, 127.91, 128.17, 128.22, 130.13, 135.35, 135.50, 144.44, 150.76, 153.14, 158.61, 163.55, 164.72, 164.77, $^{31}$P-NMR (CDCl$_3$) 147.14, 147.82.

Example 4. Synthesis of the Modified Oligonucleotides

The synthesis was performed following the standard protocol, except dmf-protected dG amidite (Glen Research) was used. Since MePizPDZdG analog is poorly soluble in acetonitrile, a mixture of dichloroethane-acetonitrile (3:1) was used as a solvent for this amidite. No other modifications to the protocol are necessary. Deprotection was done in aqueous ammonia for 5 hrs at 55°. Chromatographic purification and final postsynthetic treatment were performed according to the standard protocols (Agrawal, S. 1993).

Example 5. Stabilizing Effect of PDZ Nucleotides on DNA

Thermal denaturations of the modified and control duplexes were carried out using a CARY100 Bio UV-vis spectrophotometer, equipped with a multicell block temperature regulation unit and a fluid circulation thermal regulation enhancement (Varian, Inc.). Temperature readings were stable and accurate within 1° C. Initial temperatures, 10° C. or 80° C. depending upon the experiment, were allowed to equilibrate for at least 10 min. The rate of temperature change was set to 0.5° C./min. Sample concentrations varied between 0.2 and 2.2 OD$_{260}$ units of duplex dissolved in 1 ml of a standard PCR buffer solution, pH 8.3. Duplex melting temperatures (T$_m$) were computed from the first derivative of the Abs versus temperature plots. Three independent melting profiles were obtained at each of sample concentrations. Plots of (1/T$_m$) versus ln(C$_t$), where C$_t$ is the duplex molar concentration, were fit to a straight line, and the ΔH° and ΔS° then derived from the slope and intercept, respectively. The Gibbs free energy (ΔG°) of duplex formation was calculated from these values (Breslauer, K. 1993).

FIG. 1 provides a comparison of the thermally-induced dissociation profiles of undecamer duplex V containing a central modified base pair (blue), and its dG•dC parent (magenta). On this figure, the melting curves of 11-mer duplexes with a sequence CGTATXTATGC are shown, where X is either MePizPDZdG, or dG (control). A comparison of these curves demonstrates that incorporation of a single MePizPDZdG residue increases T$_m$ by 18.8° C.

The detailed data on the effect of the dG analogs on the melting temperature of DNA are summarized on FIG. 2.

These data demonstrate that incorporation of a single PDZdG nucleotide increase melting temperature of 11-mer DNA duplexes by 5-12 degrees, depending on the sequence context, whereas PDZdA increases melting temperature by 16 degrees. The most prominent effect was observed for MPizPDZdG nucleotide (13-19 degrees). For comparison, the data for "G-clamp" (AP-dC) nucleoside, collected in the same conditions an in the came sequence context demonstrate a significant increase of Tm in one case (12 degrees), but a modest effect (4.5 degrees) in another sequence context.

Figure 3:
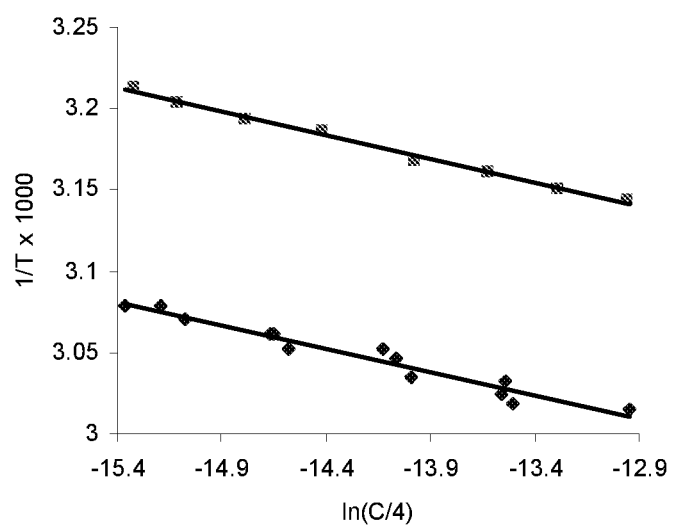
FIG. 3: Van't Hoff plots derived from UV melting curves of the duplex CGTATXTATGC/GCATACATACG (I), where X is a PDZdG nucleotide (bottom), and its canonical dG•dC parent (top).

FIG. 3 provides Van't Hoff plots derived from UV melting curves of the undecamer duplex I containing a central PDZ-dG•dC (blue), and its canonical dG•dC parent (magenta). The thermodynamic parameters of the duplex I formation are presented on the FIG. 4.

Example 6. Discrimination of DNA Mismatches by PDZ Oligonucleotides

Figure 5:
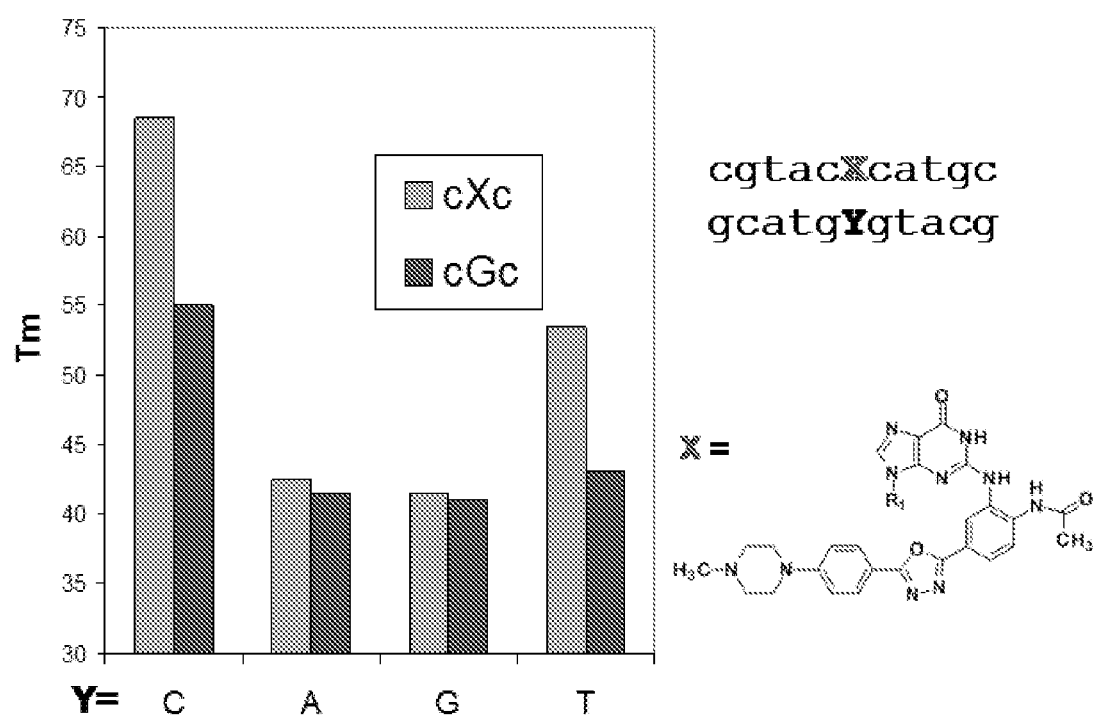
FIG. 5: Sensitivity of the PDZ base towards mismatches. Melting temperatures of perfectly matched duplex II containing PDZ-dG (the structure is shown on the right) opposite dC, dG, dA, and dT (gray-blue) vs the parent duplex (claret).

On the FIG. 5 the melting temperatures are shown of the 11-mer duplexes that contained one of four nucleoties (dC, dA, dG, or dT) opposite MePizPDZdG or dG. The data demonstrate a significant temperature decrease when a mismatched base was opposite MePizPDZdG. The temperature drop was about two times higher for the modified base than for natural dG.

Figure 6:
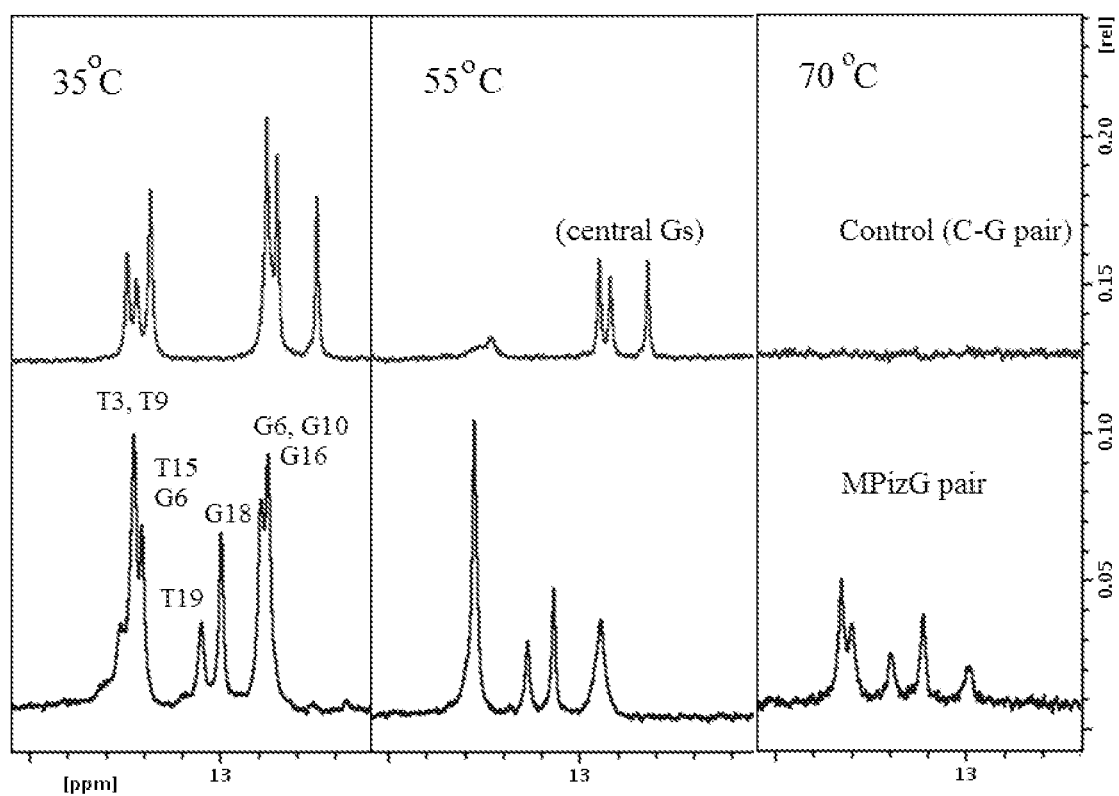
FIG. 6: NMR melting study of the effect of MePizPDZdG on the thermal stability of the DNA secondary structure. The NMR spectra of the duplex II at different temperatures are shown at the bottom, the spectra of the control (unmodified) duplex are on the top. The spectra were collected in water/$D_2O$ (9:1); only the region containing H-bond protons (A-T and G-C base pairs) are shown.

Example 7. NR Melting Study of the Effect of MePizPDZdG on the Thermal Stability of the DNA Secondary Structure In FIG. 6, the results of the NMR melting study of the undecamer DNA duplex II (see FIG. 2) are shown. The sequence of the modified strand is d(CGTACXCATGX), X is MePizPDZdG, the sequence of the complementary strand is d(GCATGCGTACG). The control duplex has the same sequence, and X is dG. The study is done in 10% D$_2$O in H$_2$O at pH 6.5. Only the region containing H-bonded protons is shown. The spectra of the duplex II are shown at the bottom, the spectra of the control duplex are on the top. It can be seem that only three central base pairs remain visible in the control duplex at 55°, whereas most non-terminal H-bonds are preserved in the duplex II. At 70°, no H-bonds are observed in the control duplex, whereas the central segment of the duplex II still contains intact H-bonds.

Advantages of Disclosed Oligonuleotides

Minor groove binder oligonucleotide adducts (see, e.g., U.S. Pat. No. 6,084,102 and references cited therein) are composed of existing minor groove binders attached to 3' and/or 5' terminus of the oligodeoxynucleotide with aliphatic linkers. These adducts have a significantly increased stability, however, they have two limitations. Firstly, the structure of these adducts allows MGB attachment only to the oligonucleotide termini, and, secondly, the stabilizing effect of the MGB is significantly sequence dependent and is much more prominent for the A-T rich sequences. In contrast, the monomers described herein efficiently stabilize DNA double helix in all sequence contexts studied, and they can be incorporated into any desirable position (or positions) of the modified oligonucleotide.

"G-clamp" nucleotide is the analog of deoxycytidine nucleoside (see, e.g. U.S. Pat. Nos. 6,005,096, 6,007,992 and references citer therein) that forms an additional hydrogen with complementary guanine and further stabilizes the base pair via stacking interactions with neighboring bases. Incorporation of a single "G-clamp" residue considerably enhances hybridization properties of the modified oligonucleotide. However, this effect is extremely sequence dependent (from 4 to 18°, see Ortega et al. 2007). Another disadvantage of the "G-clamp" is that this type monomer recognizes only guanine bases. No nucleotide analogs with comparable hybridization properties exist to pair with other nucleobases. In contrast to "G-clamp" the proposed technology is much less sensitive towards the sequence context, and it introduces both G and A analogs, thereby allowing targeting virtually any sequence motif.

Propynyl modified oligonucleotides, such as 5-propynyl-2'-deoxyuridine oligonucleotides (Ahmadian et al. 1998) have a relatively minor stabilizing effect (ca 1.8-2° per substitution). Our technology has an advantage over these in that base modifications may be used.

Sugar-phosphate backbone modifications: peptide nucleic acids (PNA) and locked nucleic acids (LNA). These oligomers are functional analogs of DNA, although their sugar-phosphate backbone is significantly modified. PNAs (see Porcheddu et al. 2005) have a significantly increased affinity towards DNA and RNA, however, they have several disadvantages. Firstly, since the stabilization is mostly due to the lack of coulombic repulsion between strands, this effect in the most prominent in low salt conditions, whereas at physiological salt concentration PNAs are much less efficient. Secondly, significant technical problem exist that are associated with low solubility of PNAs in water, their tendency to be adsorbed on various surfaces, and low membrane permeability. In contrast, the technology proposed in this document is devoid of these limitations, because the modified oligonucleotides containing the new purine analogs are structural analogs of natural DNA, so they inherit all its properties, including good solubility and adsorption on hydrophobic surfaces.

It worth mention, however, that incorporation of new PDZ purine analogs into PNAs may significantly improve the DNA binding properties of the latter, because the primary factor affecting PNA affinity towards DNA is low Coulomb repulsion. That means the addition of the modified base involved in extensive interactions with the minor groove of the PNA-DNA duplex may further increase the stability of the latter, and this effect will not be salt dependent.

With regard to LNA (see Wengel, J. et al. 2005), these oligonucleotide analogs demonstrate good hybridization properties (1 to 4° melting temperature increase per substitution), however, multiple incorporation of the LNA monomers is required to achieve an effect comparable to that of incorporation of a single PDZdA or MePizPDZdG monomer.

DISCUSSION

It has been demonstrated previously that some adducts formed between endogenously activated polyaromatic hydrocarbons and DNA lead to significant stabilization of the DNA secondary structure (Lukin, M. et al. 2011; Zaliznyak, T. et al. 2006). Systematic study of the effect of exocyclic bulky aromatic groups on the DNA stability allowed us to identify novel dG analogs that considerably improve oligonucleotide hybridization properties.

Our study demonstrated that incorporation of the nucleoside analog PDZ-dG or its analogs into synthetic oligonucleotides significantly stabilizes the duplexes formed by these oligonucleotides and a complementary DNA strand. When incorporated instead of dG, PDZ-dG analog increases dsDNA stability by 2.5-3.6 kcal/mol per modification in all sequence contexts studied. Enthalpy-entropy compensation was observed in all cases, which suggests the role of hydrophobic effects in the duplex stabilization. The stabilizing effect of PDZ-dG is comparable to the effect of G-clamp, a cytosine analog with increased affinity towards guanine (Ortega, J.-A. et al, 2007). A comparison of "G-clamp" with MePizPDZdG demonstrates that the stabilizing effect of the latter on DNA is much less dependent on GC content than the effect of "G-clamp". In addition, significant sequence dependence of its stabilizing effect, "G-clamp" works poorly in some low melting sequence contexts. I contrast, DNA stabilizing effect of PDZ analogs is especially prominent for low melting sequences, which make them an extremely useful tool for developments of various DNA probes, DNA arrays, PCR clamps and similar products.

In addition to substantial enhancement of DNA thermal stability, the PDZ-dG containing oligonucleotides demonstrate increased mismatch discrimination, especially when the mismatched base in the opposite strand is adenine or guanine. The mismatch discrimination effect of MePizPDZdG is outstanding: the decrease of melting temperature as a result of a single mismatch is ca 27°, whereas for the unmodifed DNA the temperature drop is just 14°. That makes the PDZ-dG monomer a potentially useful tool for creation of various DNA hybridization methods, especially for detection of point mutations.

The considerable DNA duplex stabilizing effect of new nucleotide analogs PDZdG, PDZdA, and especially, MePizPDZdG, makes them good complement to the "G-clamp" cytosine analog. It is especially important that the stabilizing effect of these nucleotides depend on GC-content only moderately, and, importantly, it is more prominent in A-T rich sequence context. That makes PDZ nucleotides a potentially useful tool for the design of dsDNA invading oligonucleotides, for promoter targeting, etc. The binding affinity of "G-clamp" nucleotide to the complementary DNA is strongly sequence dependent, ranging from 4 to 18 degrees (for decamer duplex) in different sequence contexts (Ortega, J.-A. et al. 2007). In contrast, we did not observe considerable sequence dependence of the effect of PDZ nucleotides, and, based on the results of our NMR studies, we see no reason to expect such dependence exists.

Incorporation of the nucleoside monomers described herein into the oligonucleotide leads to significant enhancement of their hybridization properties. For example, incorporation of a single residue MePizPDZdG into the undecamer oligodeoxynucleotide dCGTACXCATGC (where X=) increases melting temperature of the duplex with its complementary strand by 13° (from 55° to 68°). The stabilizing effect of the modification is only moderately sequence dependent, and it is more significant for the AT rich DNA segments, which are known to have lower thermodynamic stability. Increased stability of duplexes allow usage of shorter oligodeoxynucleotides, which means the contribution of individual base pairs into the duplex stability increases, thereby increasing the effect of a single base-pair mismatch.

In addition to substantial enhancement of DNA thermal stability, the modified oligonucleotides demonstrate increased mismatch discrimination, especially when the mismatched base in the opposite strand is adenine or guanine. That makes the PDZ-dG monomer a potentially useful tool for creation of various DNA hybridization methods, especially for detection of point mutations, single nucleotide polylnorphism, microarray technologies, nanofabrication, etc.

A number of the analogs described in this invention, are strongly fluorescent, which makes them a potent tool for various fluorescence based detection assays.

Finally, all above described analogs have strong absorption in near UV and/or visible range, which makes them potent quenchers for creation of molecular beacon probes.

Possible application of new nucleotides is the design of oligonucleotide probes for detection of point mutations, because incorporation of a single PDZ moiety near the potential mutation site increases the relative energetic contribution of the mutation locus into the overall duplex stability, which will lead to increased mismatch discrimination in PCR clamp experiments, oligonucleotide arrays, etc.

In addition, the PDZ modification can be used in combination with many existing DNA backbone modification, including PNA, which may give a new impetus to the development of novel DNA targeting oligonucleotides.

REFERENCES

Agrawal, S. (Editor) Protocols for Oligonucleotides and Analogs, Human Press, 1993.
Ahmadian et al. (1998) A comparative study of the thermal stabilityy of oligodeoxyribonucleotides containing 5-substituted-2'-deoxyuridines. Nucl. Acids Res. 26 (13): 3127-3135).
Breslauer, K. in Protocols For Oligonucleotide Conjugates: Synthesis and Analytical Techniques S. Agrawal (Editor), Humana Press, 1993.
Lin, K.-Y.; Matteucci, M. (1998) A cytosine analogue capable of clamp-like binding to a guanine in helical nucleic acids. J. Am. Chem. Soc. 120(33), 8531-8532.
Lukin M., Zaliznyak T., Johnson F., de los Santos C R. (2011) Incorporation of 3-Aminobenzanthrone into 2'-Deoxyoligonucleotides and Its Impact on Duplex Stability. J. Nucl. Acids. 521035.
Nielsen, P. E. et al. (1991) Sequence-selective recognition of DNA by strand displacement with a thymine-substituted polyamide, Science 254 1497-1500.
Ortega J.-A., Blas J R, Orozco M, Grandas A., Pedroso E., Robles J. (2007) Binding Affinities of Oligonucleotides and PNAs Containing Phenoxazine and G-Clamp Cytosine Analogues Are Unusually Sequence-Dependent. Org. Lett. 9, 4503-4506.
Porcheddu et al. (2005) Peptide Nucleic Acids (PNAs), A Chemical Overview. Current Medicinal Chemistry, 12, 2561-2599.
U.S. Pat. No. 6,084,102, issued Jul. 4, 2000.
U.S. Pat. No. 6,005,096, Dec. 21, 1999.
U.S. Pat. No. 6,007,992, issued Dec. 28, 1999.
Wengel, J. et al. (1999) Synthesis of 3'-C- and 4'-C-branched oligodeoxynucleotides and the development of locked nucleic acid (LNA). Acc. Chem. Res. 32:301-10.
Zaliznyak T., Bonala R., Johnson F., de los Santos C. (2006) Structure and Stability of Duplex DNA Containing the 3-(Deoxyguanosin-N2-yl)-2-acetylaminofluorene (dG(N2)-AAF) Lesion: A Bulky Adduct that Persists in Cellular DNA. Chem. Res. Toxicol. 19, 745-752.

What is claimed is:

1. A compound having the structure:

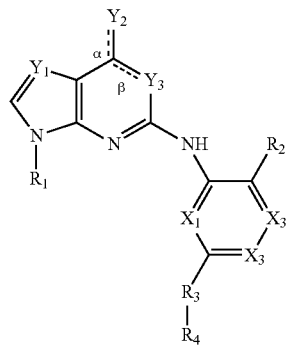

wherein
a is a bond and is present or absent,
b is a bond and is present or absent,
wherein when a is present, then b is absent and when b is present, then a is absent;
$Y_1$ is N or $CR_5$,
wherein $R_5$ is aminoalkyl;
$Y_2$ is O, $NH_2$, $NHR_6$ or $NH-PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_1$ is a substituted tetrahydrofuran;
$R_2$ is H, $NH_2$ or NHC(O)—$R_7$,
wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

2. The compound of claim 1, wherein
a is a bond and is present or absent,
b is a bond and is present or absent,
wherein when a is present, then b is absent and when b is present, then a is absent;
$Y_2$ is N or $CR_5$,
wherein $R_5$ is aminoalkyl;
$Y_2$ is O, $NH_2$, $NHR_6$ or $NH-PG_1$,
wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_1$ is a substituted tetrahydrofuran;
$R_2$ is NHC(O)—$R_7$,
wherein $R_7$ is alkyl;
$R_3$ is present or absent and when present is —C(O)—, —C(O)NH—, —NH(O)C— or —N=N—; and
$R_4$ is a substituted five or six-membered aryl or heteroaryl, wherein the substitution on the six-membered aryl is other than fluorine substitution.

3. The compound of claim 1, wherein $Y_1$ is N.

4. The compound of claim 1, wherein $Y_1$ is $CR_5$, wherein $R_5$ is aminoalkyl.

5. The compound of claim 1 having the structure:

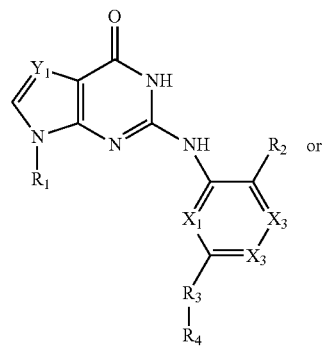

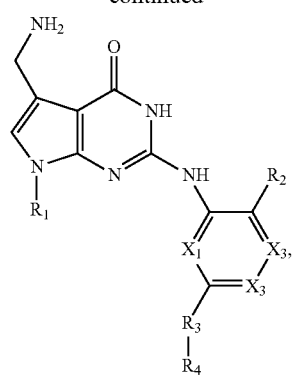

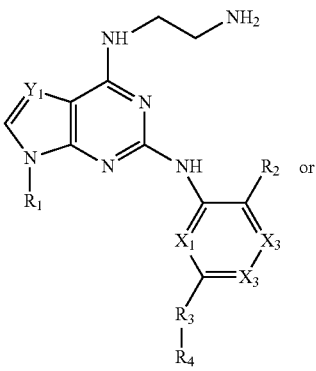

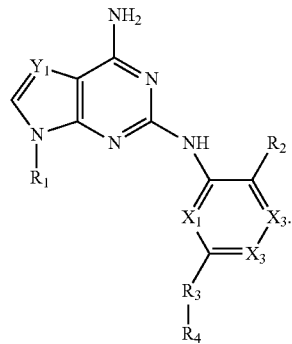

6. The compound of claim 1, wherein one of $X_1$, $X_2$ or $X_3$ is N and the other two of $X_1$, $X_2$ or $X_3$ are CH.

7. The compound of claim 1, wherein $R_3$ is absent.

8. The compound of claim 1, wherein $R_3$ is present and is —C(O)NH—, —NH(O)C— or —N=N—.

9. The compound of claim 1, wherein $R_4$ has the structure:

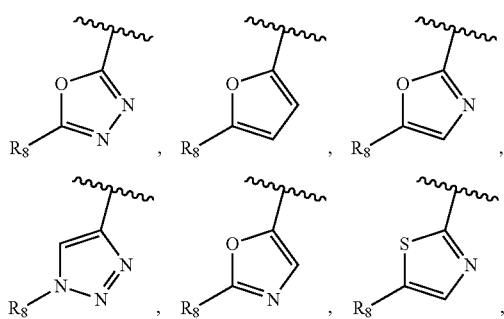

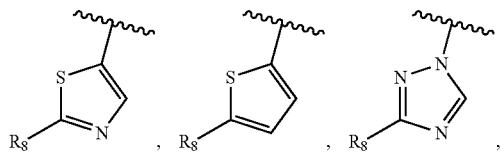

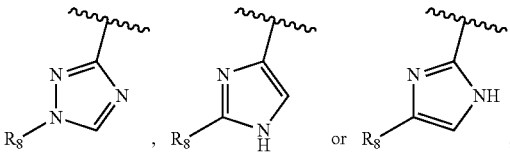

wherein $R_8$ is alkyl, alkenyl, alkynyl, aryl, substituted aryl, heteroaryl, substituted heteroaryl, heteroalkyl or heterocycloalkyl.

10. The compound of claim 9, wherein $R_8$ has the structure:

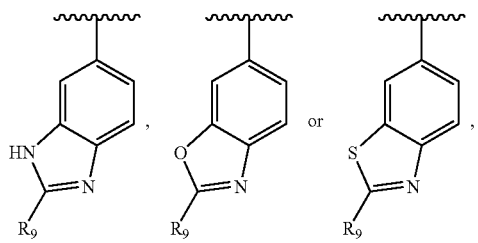

wherein $R_9$ is alkyl, aryl, substituted aryl, heteroaryl, substituted heteroaryl or heterocycloalkyl, or has the structure:

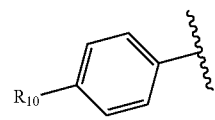

wherein $R_{10}$ is alkyl, aminoalkyl, aryl, substituted aryl, heteroaryl, substituted heteroaryl or heterocycloalkyl.

11. The compound of claim 1, wherein $R_4$ has the structure:

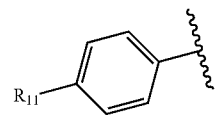

wherein $R_{11}$ is alkyl, aminoalkyl, aryl, substituted aryl, heteroaryl, substituted heteroaryl or heterocycloalkyl.

12. The compound of claim 1 having the structure:
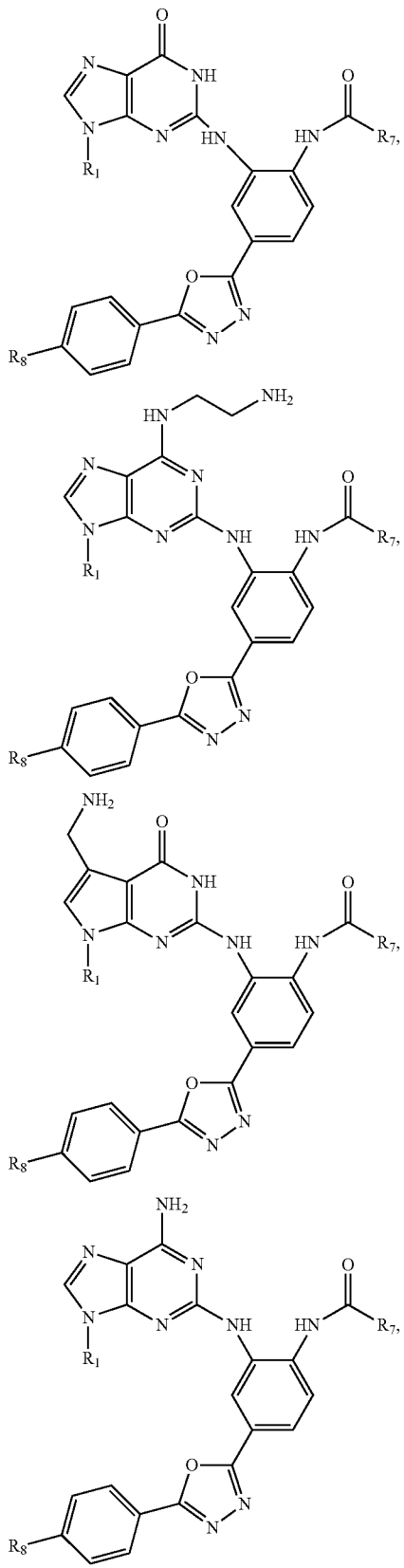
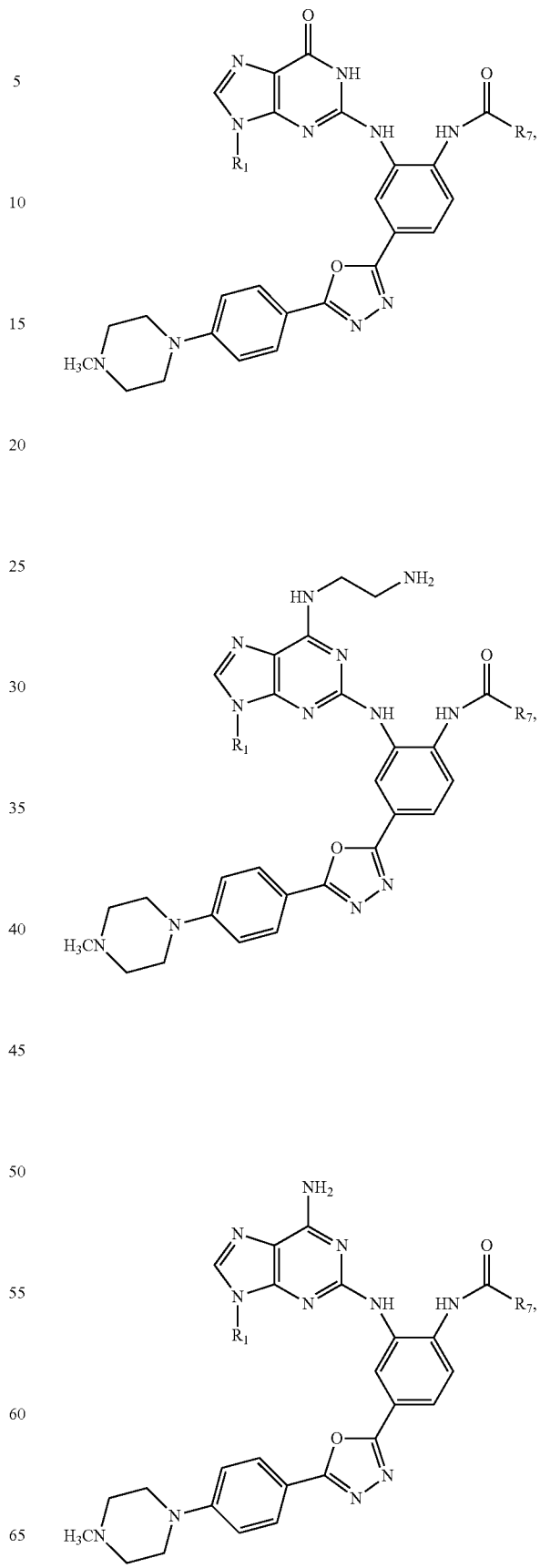

73
-continued
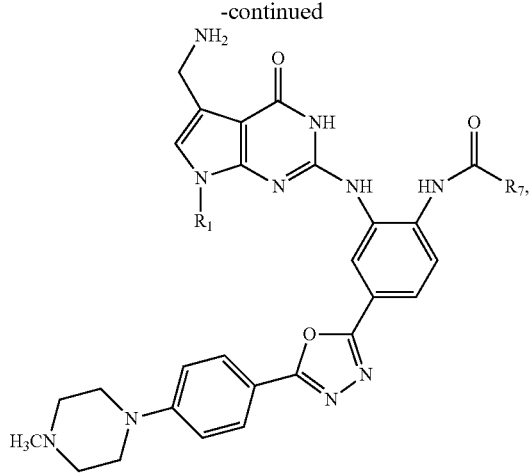
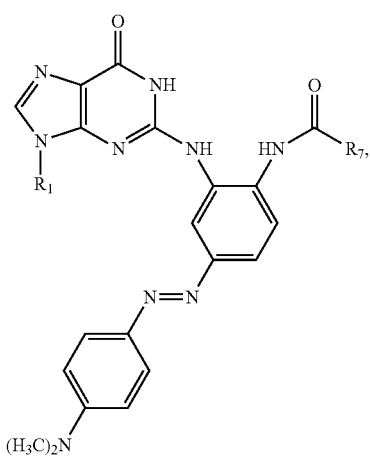
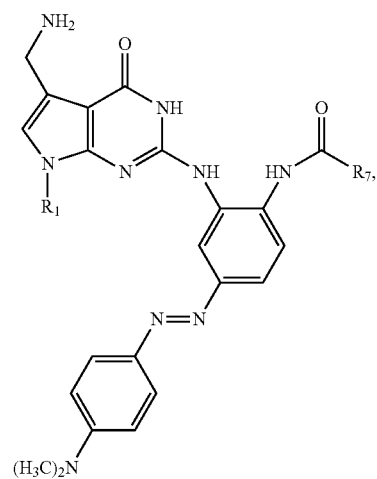
74
-continued
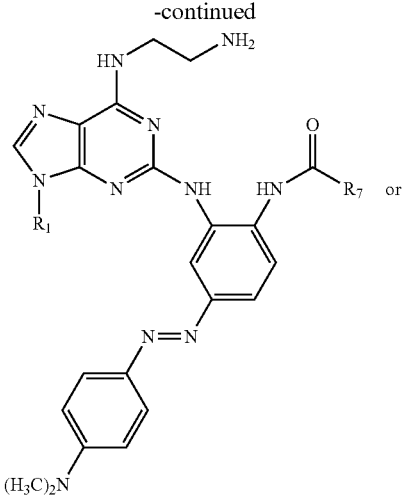 or
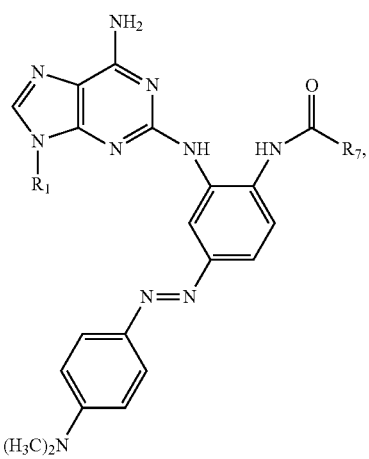
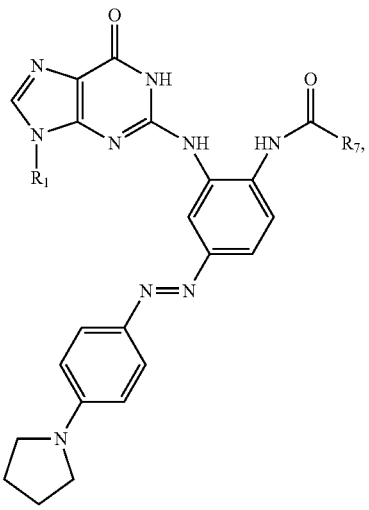

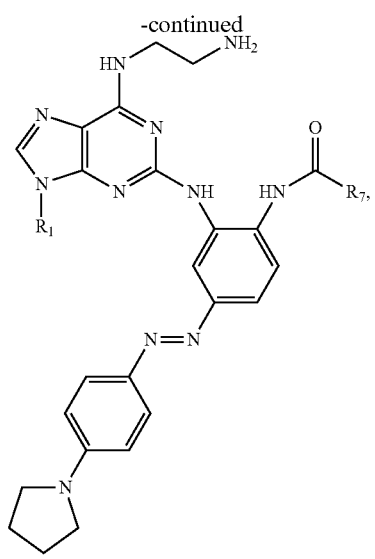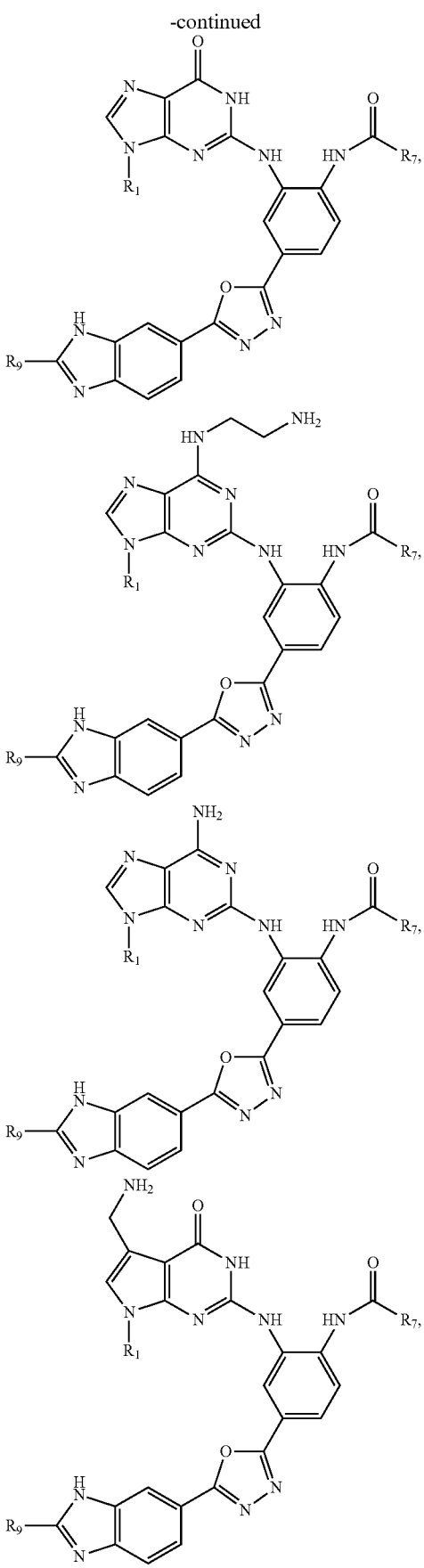

-continued

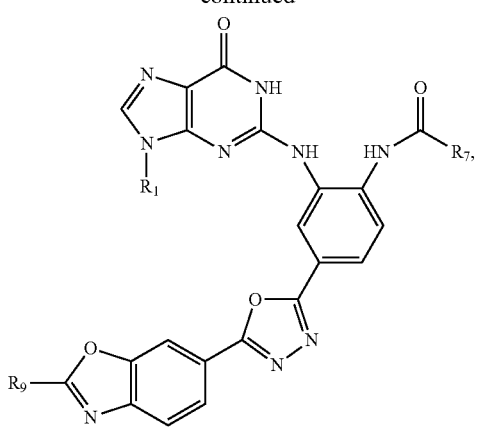

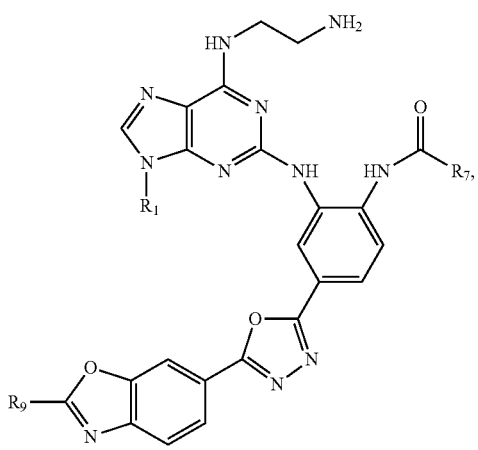

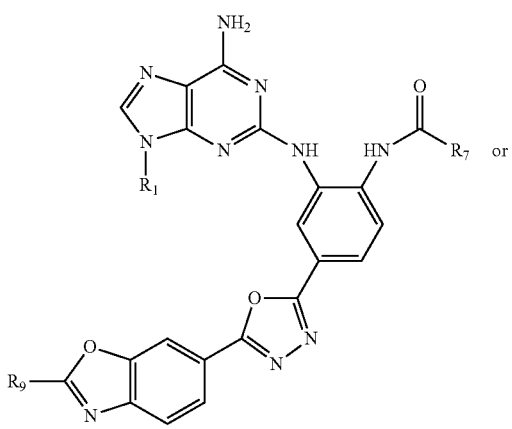

-continued

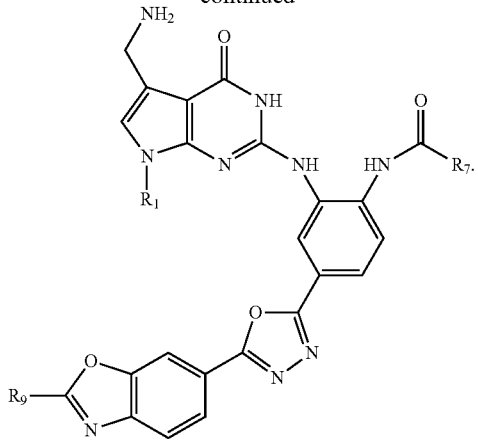

13. The compound of claim 1, wherein $R_1$ has the structure:

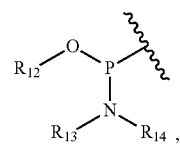

wherein $R_9$ is H or $PG_2$;

$R_{10}$ is H or $PG_3$;

$R_{11}$ is H, OH or O-$PG_4$, wherein $PG_2$, $PG_3$ and $PG_4$ are each, independently, a suitable hydroxyl protecting group.

14. The compound of claim 13, wherein $R_9$ is H or $PG_2$, wherein the $PG_2$ is a trityl, monomethoxy trityl (MMT), dimethoxytrityl (DMT), acetyl benzoyl, isobutyl, or 5'-O-(α-methyl-6-nitropiperonyloxycarbonyl) (MeNPOC); and $R_{11}$ is H, OH or O—$PG_4$, wherein the $PG_4$ is a tert-butyldimethylsilyl (TBDMS or TBS), triisopropylsilyloxymethyl (TOM), bis(2-acetoxyethoxy)methyl (ACE) or thiomorpholine-4-carbothioate (TC).

15. The compound of claim 13, wherein $R_{10}$ is H or $PG_3$ wherein the $PG_3$ is a phosphoramidite group.

16. The compound of claim 15, wherein $R_{10}$ has the structure:

wherein $R_{12}$ is cyanoethyl, trichloroethyl, methyl, phenyl, benzyl, dimethyltrichloroethyl, chlorophenyl, 2-phenylethyl or a substituted aryl; and $R_{13}$ and $R_{14}$ are each isopropyl or methyl or combine to form a morpholino.

17. The compound of claim 16, wherein R₁₀ has the structure:
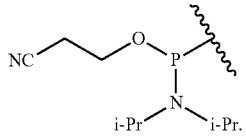
18. The compound of claim 1 having the structure:
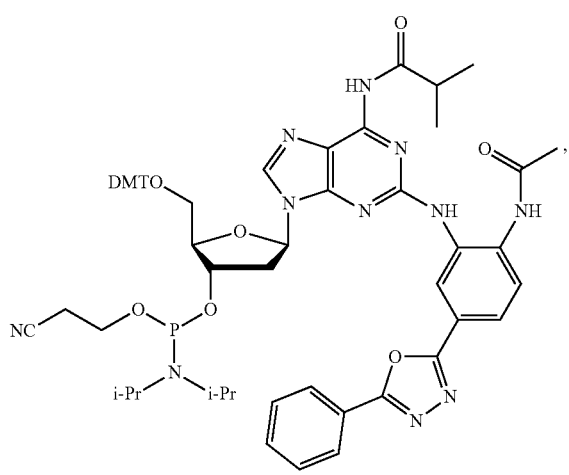
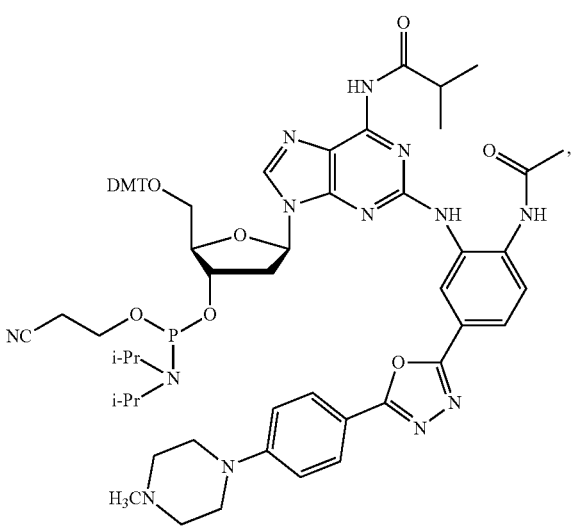
-continued
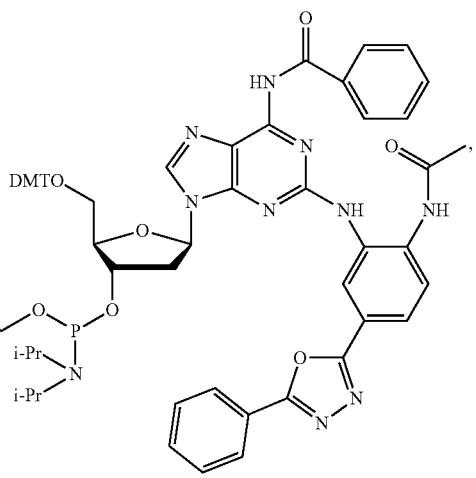
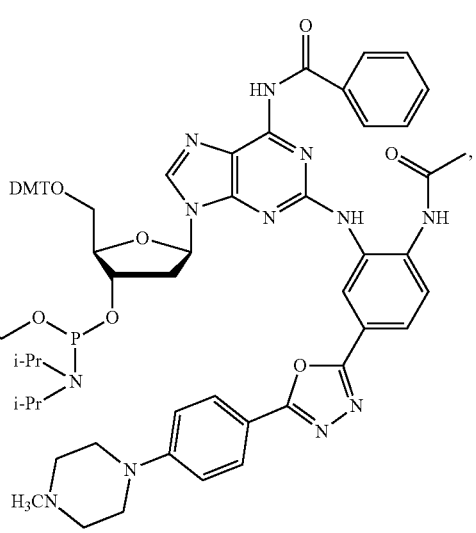
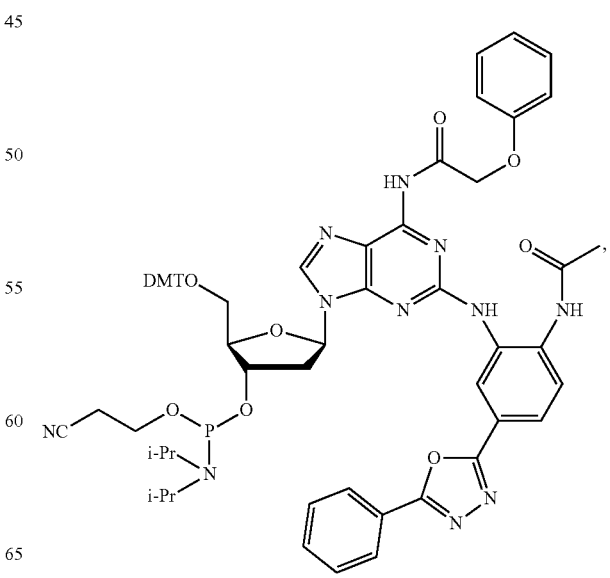

81
-continued
82
-continued
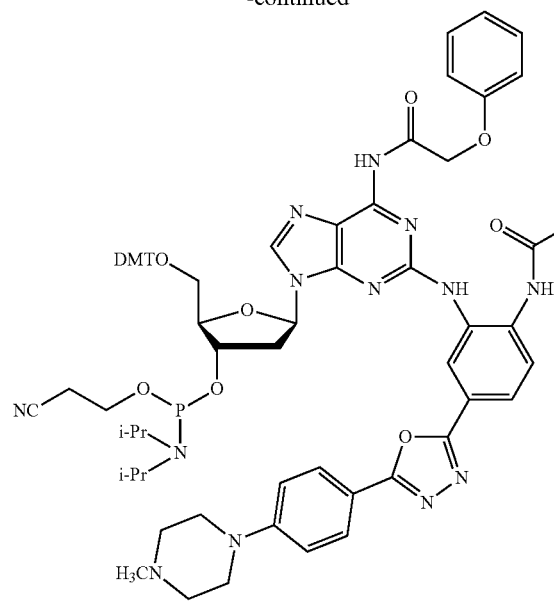
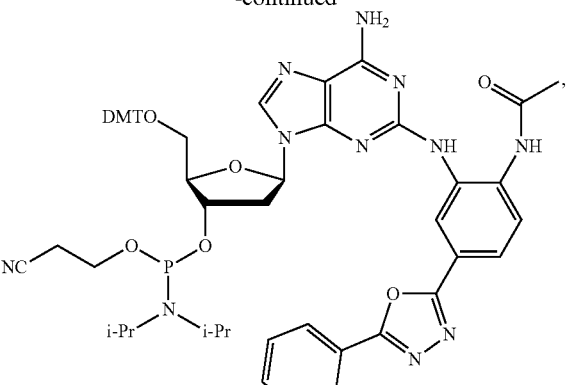

-continued

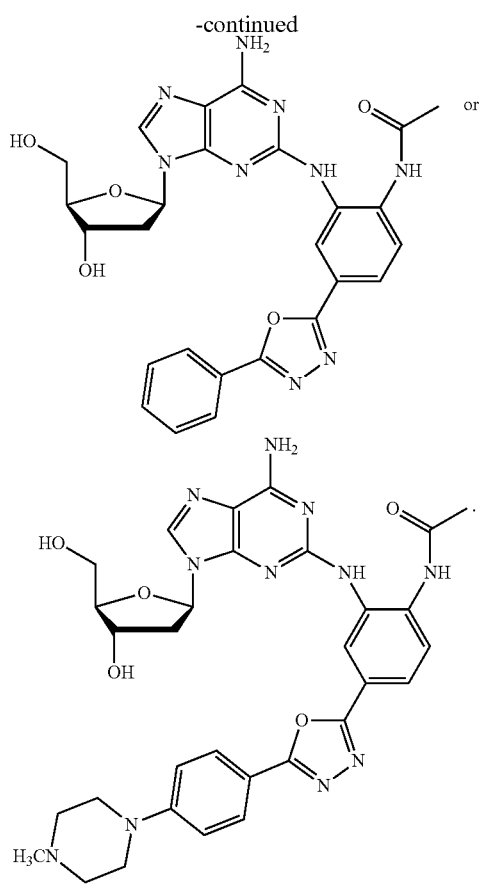

19. A nucleotide or, nucleoside, oligonucleotide or polynucleotide, or peptide nucleic acid containing the following structural moiety:

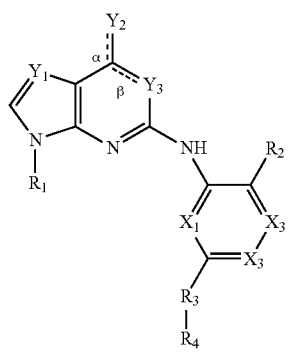

wherein
a is a bond and is present or absent,
b is a bond and is present or absent,
  wherein when a is present, then b is absent and when b is present, then a is absent;
$Y_1$ is N or $CR_5$,
  wherein $R_5$ is aminoalkyl;
$Y_2$ is O, $NH_2$, $NHR_6$ or $NH-PG_1$,
  wherein $R_6$ is alkyl, aminoalkyl or —C(O)-alkyl, and $PG_1$ is a suitable amine protecting group;
$Y_3$ is N or NH;
$X_1$ is N or CH;
$X_2$ is N or CH;
$X_3$ is N or CH;
$R_2$ is H, $NH_2$ or NHC(O)—$R_7$,
  wherein $R_7$ is alkyl, aryl, alkylaryl or aminoalkyl;
$R_3$ is present or absent and when present is —C(O)—, —C(O)NH—, —NH(O)C— or —N=N—; and
$R_4$ is a substituted five or six-membered aryl or heteroaryl,
  wherein the substitution on the six-membered aryl is other than fluorine substitution.

20. The nucleotide, nucleoside, oligonucleotide, polynucleotide or peptide nucleic acid of claim 19 wherein the structural moiety has the structure:

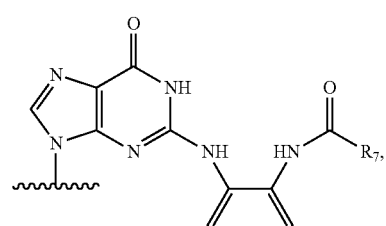

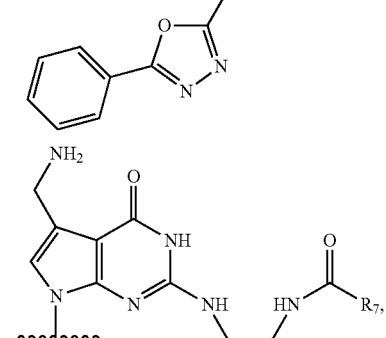

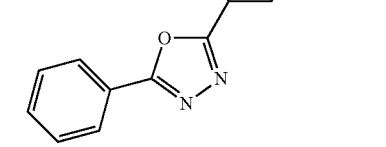

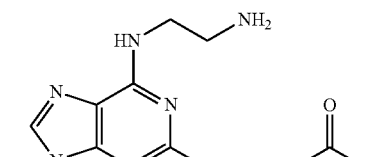

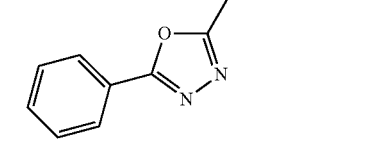

85
-continued
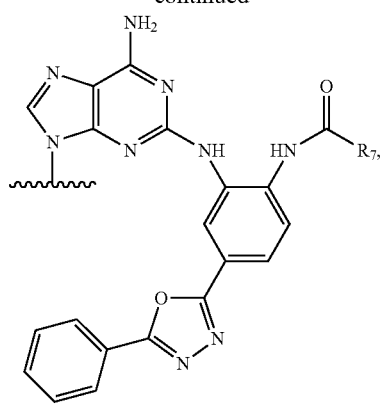
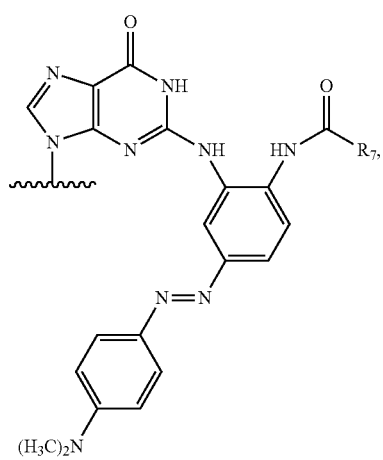
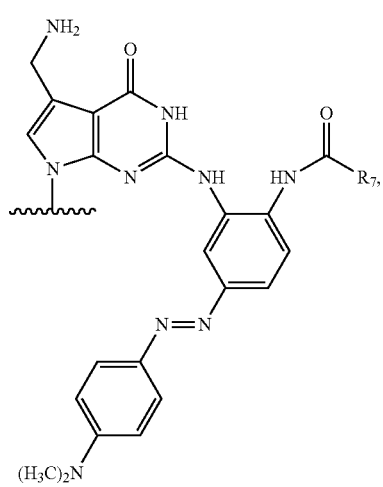
86
-continued
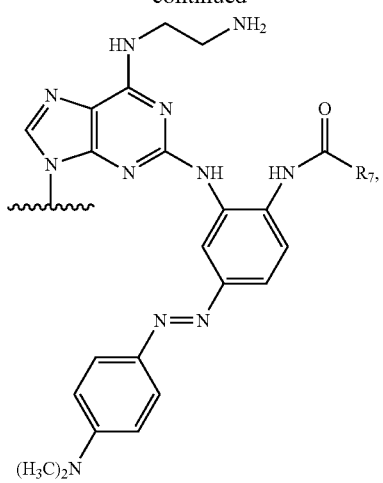
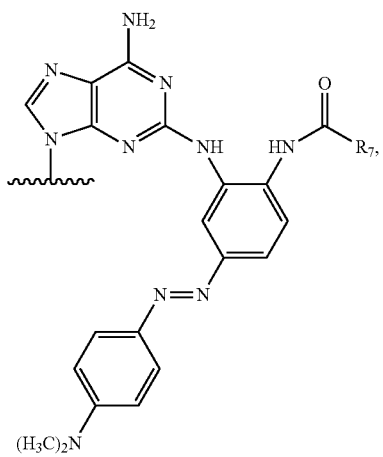
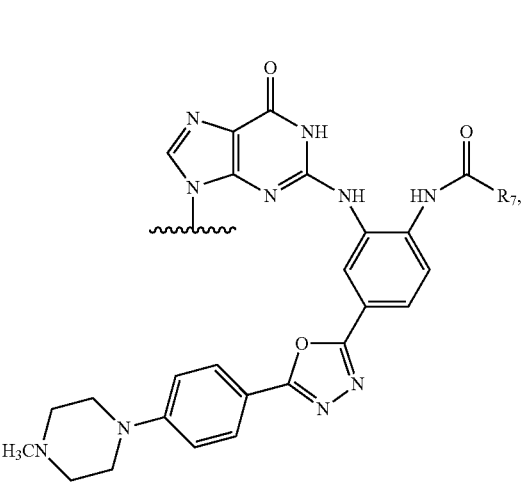

87
-continued
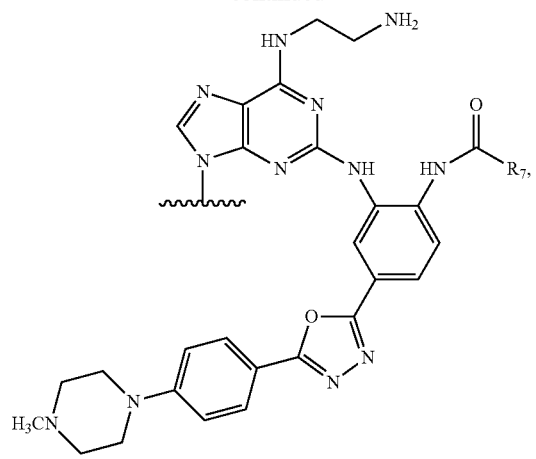
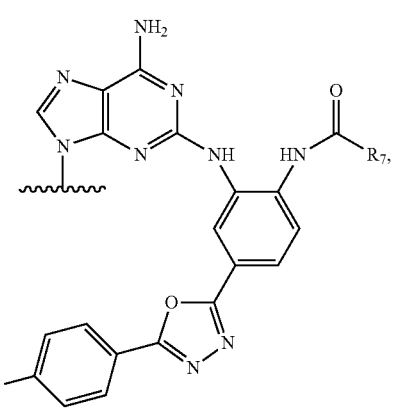
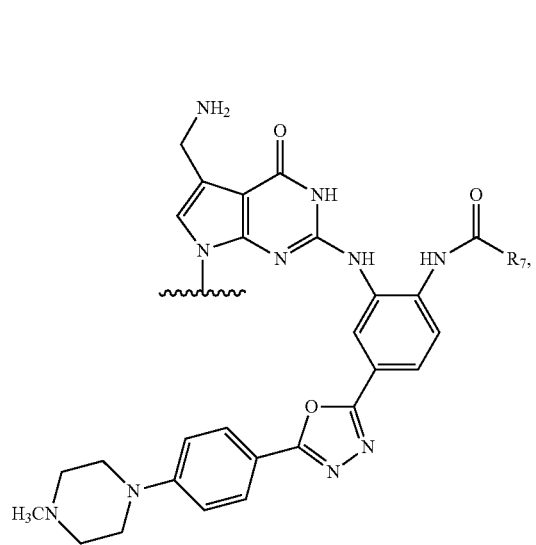
88
-continued
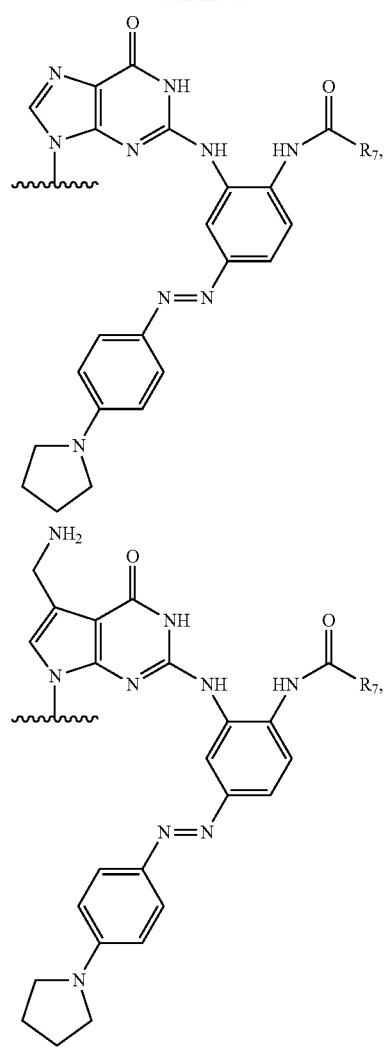
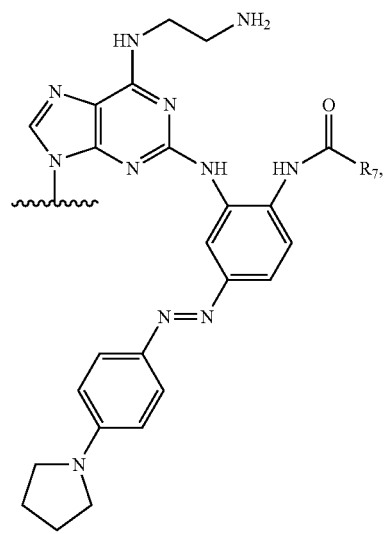

-continued
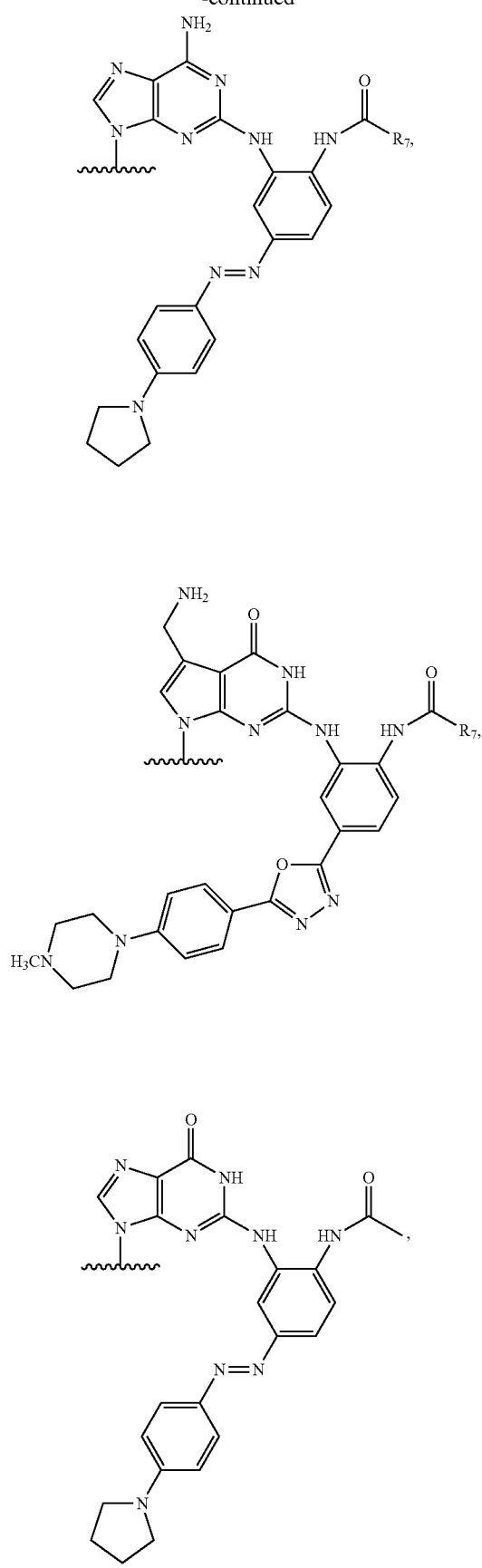
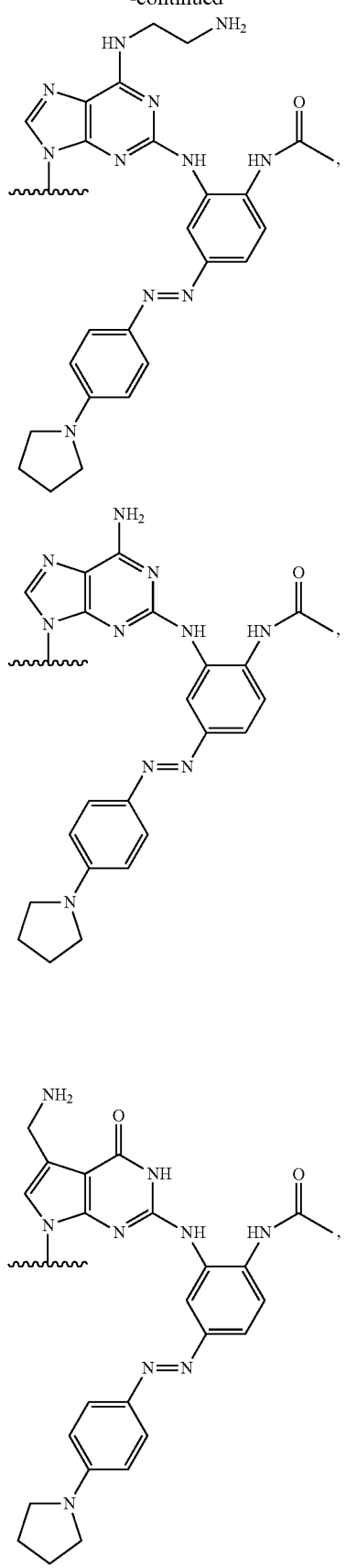

91
-continued
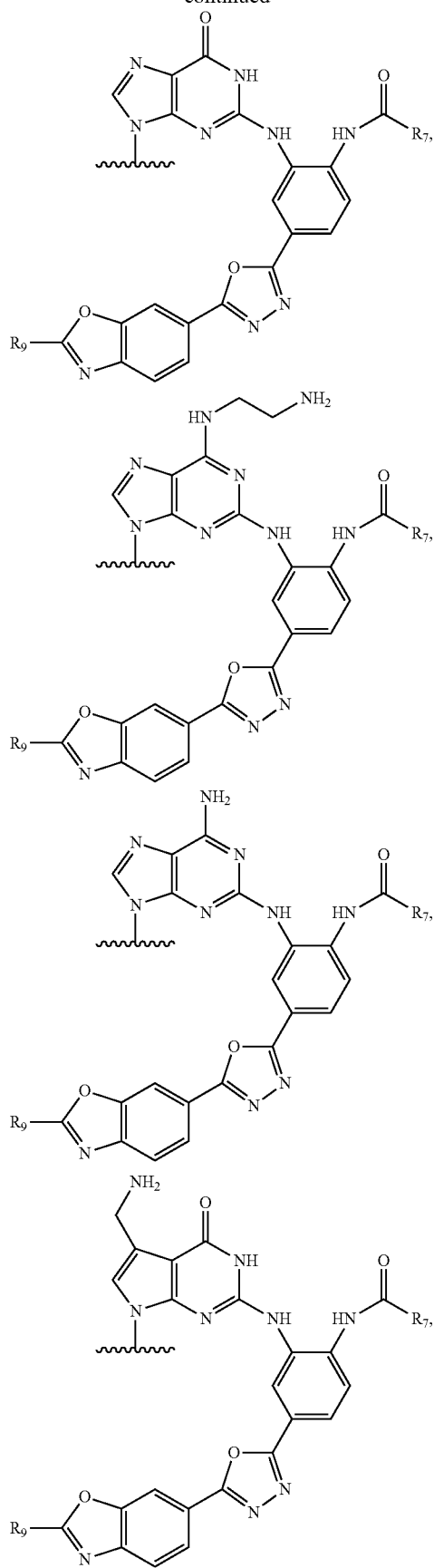
92
-continued
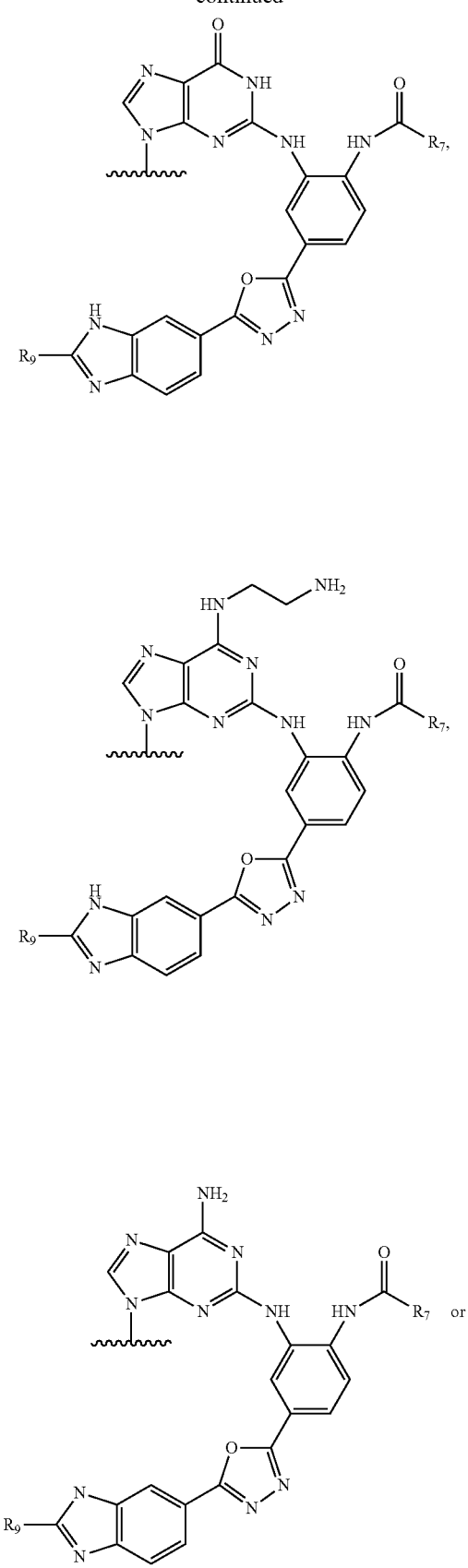

-continued
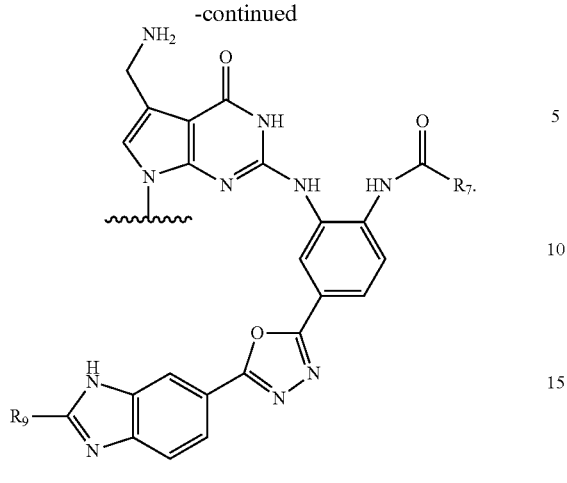
* * * * *